(12) United States Patent
Calhoun et al.

(10) Patent No.: US 10,851,360 B2
(45) Date of Patent: *Dec. 1, 2020

(54) METHODS OF PURIFYING RECOMBINANT ALPHA-GALACTOSIDASE A

(71) Applicant: RESEARCH FOUNDATION OF THE CITY UNIVERSITY OF NEW YORK, New York, NY (US)

(72) Inventors: David H. Calhoun, Leonia, NJ (US); Abass Abdullahi, New York, NY (US)

(73) Assignee: Research Foundation of the City University of New York, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/912,075

(22) Filed: Mar. 5, 2018

(65) Prior Publication Data
US 2018/0362947 A1    Dec. 20, 2018

Related U.S. Application Data

(63) Continuation of application No. 14/732,662, filed on Jun. 5, 2015, now Pat. No. 9,909,113.

(60) Provisional application No. 62/011,399, filed on Jun. 12, 2014.

(51) Int. Cl.
*C12N 9/40* (2006.01)
*B01D 15/38* (2006.01)

(52) U.S. Cl.
CPC ....... *C12N 9/2465* (2013.01); *B01D 15/3814* (2013.01); *C12Y 302/01022* (2013.01)

(58) Field of Classification Search
None
See application file for complete search history.

(56) References Cited

U.S. PATENT DOCUMENTS

| 6,210,666 B1 | 4/2001 | Miyamura |
| 7,452,697 B2 | 11/2008 | Luo et al. |
| 9,909,113 B2 * | 3/2018 | Calhoun .............. C12N 9/2465 |

OTHER PUBLICATIONS

Zhang et al., "Fermentation Strategies for Recombinant Protein Expression in the Methylotrophic Yeast *Pichia pastoris*", Biotechnol. Biopreocess Eng. 2000, 5: 275-287.
Yasuda et al., "Efficient and Rapid Purification of Recombinant Human α-galactosidase A by Affinity Column Chromatography", Protein Expression and Purification 2004, 37: 499-506.
Soper et al., "Elution of Tightly Bound Solutes From Concanavalin A Sepharose Factors Affecting The Desorption of CottonMouth Venom Glycoproteins", Journal of Chromatography A 2007, 1154: 308-318.
Miyamura et al., A Carboxy-terminal Truncation of Human α-galactosidase A in a Herterozygous Female with Fabry Disease and Modification of the Enzymatic Activity by the Carboxy-terminal Domain 1996, 98(8): 1809-1817.
Chen et al., "Expression and Characterization of Glycosylated and Catalytically Active Recombinant Human-Galactosidase A Produced in Pichia pastoris", Protein Expression and Purification 2000: 472-484.

\* cited by examiner

*Primary Examiner* — Christian L Fronda
(74) *Attorney, Agent, or Firm* — Hoffmann & Baron, LLP

(57) ABSTRACT

In one embodiment, the invention provides a method of purifying recombinant alpha-galactosidase A. The method includes obtaining a lysate from cells recombinantly expressing alpha-galactosidase A grown in a cell culture medium having non-precipitating phosphate; contacting said lysate with a first chromatography media that binds α-D-mannopyranosyl or α-D-glucopyranosyl; eluting alpha-galactosidase A from the first chromatography media to generate a first eluate having alpha-galactosidase A, wherein said eluting includes at least one elution pause between 4 and 16 hours; contacting the first eluate with a second chromatography media that binds galactose binding proteins; and eluting alpha-galactosidase A from said second chromatography media to generate a second eluate containing said recombinant alpha-galactosidase A.

9 Claims, 21 Drawing Sheets

Specification includes a Sequence Listing.

FIG. 9A

| | Band ID | MW kDa | I% |
|---|---|---|---|
| WT | B1 | 94.6 | 67 |
| | B2 | 49.7 | 25 |
| | B3 | 39.7 | 2 |
| | B4 | 33.9 | 1 |
| | B5 | 19 | 2 |
| | B6 | 13.6 | 2 |
| Δ2 | C1 | 137 | 7 |
| | C2 | 50.6 | 69 |
| | C3 | 41.3 | 10 |
| | C4 | 36.5 | 7 |
| | C5 | 21.1 | 7 |
| Δ4 | D1 | 160 | 11 |
| | D2 | 70 | 55 |
| | D3 | 51.7 | 30 |
| | D4 | 20 | 5 |
| Δ6 | E1 | 146 | 31 |
| | E2 | 92.8 | 6 |
| | E3 | 69.5 | 7 |
| | E4 | 62.6 | 8 |
| | E5 | 51.1 | 37 |
| | E6 | 41.7 | 6 |
| | E7 | 34.8 | 5 |
| Δ8 | F1 | 72.2 | 16 |
| | F2 | 51.2 | 71 |
| | F3 | 40 | 13 |
| Δ10 | G1 | 147 | 32 |
| | G2 | 64.5 | 38 |
| | G3 | 49.9 | 28 |
| | G4 | 33.6 | 2 |

Purification table for 39.X.xls

| Step | Aliquot # | Contents | units/ml | % | mg/ml | units | ml | mg | Specific Activity | Fold |
|---|---|---|---|---|---|---|---|---|---|---|
| 1 | 39.3 | Supernatant PC626 after difiltration + Buffer exchange | 304,800 | 100 | 25.0 | 133,502,400 | 438 | 10,928 | 12,216 | 1.0 |
| 2 | 39.6 | Con A pool (after buffer exchange) + AC | 202,650 | 22.8 | 0.919 | 30,397,500 | 150 | 138 | 220,511 | 18.1 |
| 3 | 39.15 | Thiogal pool (before buffer exchange) | 65625 | 11.8 | 0.0174 | 15750000 | 240 | 4,176 | 3,771,552 | 308.7 |

SEQUENCE LISTING

<160> NUMBER OF SEQ ID NOS: 5

<210> SEQ ID NO 1
<211> LENGTH: 21
<212> TYPE: DNA
<213> ORGANISM: Artificial Sequence

```
<220> FEATURE:
<223> OTHER INFORMATION: synthetic sequence

<400> SEQUENCE: 1
gactggttcc aattgacaag c                                              21

<210> SEQ ID NO 2
<211> LENGTH: 21
<212> TYPE: DNA
<213> ORGANISM: Artificial Sequence
<220> FEATURE:
<223> OTHER INFORMATION: synthetic sequence

<400> SEQUENCE: 2
ggaaatggca ttctgacatg c                                              21

<210> SEQ ID NO 3
<211> LENGTH: 21
<212> TYPE: DNA
<213> ORGANISM: Artificial Sequence
<220> FEATURE:
<223> OTHER INFORMATION: synthetic sequence

<400> SEQUENCE: 3
tactattgcc agcattgctg c                                              21

<210> SEQ ID NO 4
<211> LENGTH: 16
<212> TYPE: DNA
<213> ORGANISM: Artificial Sequence
<220> FEATURE:
<223> OTHER INFORMATION: synthetic sequence

<400> SEQUENCE: 4
gtaaaacgac ggccag                                                    16

<210> SEQ ID NO 5
<211> LENGTH: 17
<212> TYPE: DNA
<213> ORGANISM: Artificial Sequence
<220> FEATURE:
<223> OTHER INFORMATION: synthetic sequence

<400> SEQUENCE: 5
caggaaagag ctatgac                                                   17
```

METHODS OF PURIFYING RECOMBINANT ALPHA-GALACTOSIDASE A

CROSS-REFERENCE TO RELATED APPLICATIONS

This application is a continuation application of application Ser. No. 14/732,662, filed Jun. 5, 2015, which claims priority from U.S. Provisional Application No. 62/011,399, filed on Jun. 12, 2014, all of which is incorporated herein by reference.

INCORPORATION OF SEQUENCE LISTING

Incorporated herein by reference in its entirety is the Sequence Listing for the application. The Sequence Listing is disclosed on a computer-readable ASCII text file titled, "Sequence_Listing_1038-142CON.txt", created on Oct. 16, 2020. The sequence_listing.txt file is 1.3 KB in size.

This invention was made with government support under grant number NIH/NCRR/RCMI Grant G12-RR03060 awarded by the National Institutes of Health. The government has certain rights in the invention.

BACKGROUND OF THE INVENTION

Mutations in the αGal gene result in the sphingolipidosis named Fabry disease [1]. The enzymatic defect is inherited as an X-linked disorder and is associated with a progressive deposition of the glycosphingolipids, including globotriaosylceramide, galabioasylceramide, and blood group B substance. In affected males this leads to early death due to occlusive disease of the heart, kidney, and brain.

De Duve [2] first suggested that ERT might be a successful approach to the treatment of lysosomal storage defects such as Gaucher's and Fabry disease. For Gaucher's disease, ERT produced unequivocal clinical responses [3, 4] that were subsequently confirmed by others [5-7]. Classical Fabry disease patients lack detectable levels of αGal [1] so it should not be surprising that more than 80% of Fabry patients treated with agalsidase-beta [8] and more than 50% treated with agalsidase-alfa [9] developed an immune response. The antibodies produced are primarily of the IgG class and a fraction of the antibodies appear to exhibit neutralizing properties. These antibodies have been associated with an increase in urinary globotriaosylceramide levels due to the uptake of immune-enzyme complexes by granulocytes in the bloodstream and macrophages in the tissues [10-12].

ERT for Fabry disease patients was initially undertaken for males with the classic form of the disease (no detectable αGal activity) in a variety of clinical trials [8, 9, 13-16], but therapy is now also underway for heterozygous females with Fabry disease [17-19] and is under consideration for children [20-22] and adults with atypical (low levels of enzyme) Fabry disease [23]. The two products used for ERT in Fabry disease patients have been compared [24]. The pattern of glycosylation on αGal has been analyzed [25] and its importance for activity [26] and uptake by cells has been established [27, 28]. The limitations of current approaches for ERT for Fabry disease and the need for improved techniques have been discussed [10, 29, 30]. Efforts for gene therapy for Fabry disease are underway [31-38] and molecular chaperones are under investigation for specific alleles [39-41]. Substrate reduction therapy as an augmentation to ERT has been evaluated [42]. There are several reviews on the general topic of ERT for lysosomal storage diseases [43-47].

Expression of the human αGal has been reported in *Escherichia coli* [48], baculovirus [49, 50] Chinese hamster ovary cells [51] and human foreskin fibroblasts [52]. The highest levels of heterologous αGal expression were observed in *Pichia pastoris* [53]. Recombinant αGal has also been produced in a modified strain of *Saccharomyces cerevisiae* that synthesized glycoprotein lacking the outer chain of N-glycan, a structure that is specific to yeast but not humans [28, 54]. When this αGal was introduced into Fabry patient fibroblasts or a Fabry mouse model, there was hydrolysis of accumulated substrates [28, 54]. The methylotrophic yeast *P. pastoris* is the most highly developed of a small group of alternative yeast species chosen for their advantages over *S. cerevisiae* as expression hosts [55, 56]. Two attributes critical in its selection are the existence of well-established fermentation methods and the presence of the tightly regulated methanol-inducible promoter. AOX expression is undetectable by enzyme assay or mRNA production in cells cultured on carbon sources such as glycerol, but constitutes up to 30% of total soluble protein in methanol-grown cells. Heterologous genes under the control of the PAOX1 promoter can be maintained in an expression-off mode on a non-methanolic carbon source in order to minimize expression of potentially toxic heterologous proteins during cell growth. The *P. pastoris* expression system has now been successfully used to produce a number of heterologous proteins at commercially useful concentrations [57].

Lysosomal enzymes such as αGal are glycoproteins that are modified in the Golgi to contain N- or O-linked carbohydrate structures [58]. The human αGal is glycosylated at Asp residues 139, 193, and 215 [26] with branched carbohydrate structures that vary in composition and sequence depending upon the host species and tissue type [25]. For example, the enzyme purified from humans contains variable amounts (5-15%) of asparagine linked complex and high mannose oligosaccharide chains [1]. Consequently, multiple forms are present in SDS gels and in isoelectric focusing experiments that correspond to the plasma and various tissue forms. The Carboxyl-Terminal Truncations of the Human α-Galactosidase A recombinant human αGal preparations used therapeutically are produced in human and CHO cells and these have distinct glycosylation patterns and differ in levels of sialic acid and mannose-6-phosphate [24]. The recombinant αGal produced in insect cells [49, 50] and in *P. pastoris* [53] contain variable levels of mostly complex and high mannose side chains, respectively. Glycoproteins produced in *P. pastoris* typically contain from 6 to 14 mannose units (Man6-GlcNac2 to Man14GlcNac2) that sometimes produces a Gaussian-like distribution of oligo-mannosides that may center near Man12GlcNac2 to Man13GlcNac2 [59].

These carbohydrate moieties serve a structural and functional role. For example, it has been demonstrated that glycosylation, particularly at Asn-215, is required for enzyme solubility [26]. Also, uptake of the enzyme by cells in vivo is affected by terminal mannose-6-phosphate residues on the enzyme [27], and the 10-12 sialic acid residues on the plasma form of the enzyme accounts for the prolonged circulatory half-life of the enzyme compared to the tissue form with only one or two sialic acid residues [60]. The identification of these multiple forms as derivatives of the same protein in purified enzyme preparations can conveniently be monitored by treatment with specific N-glycosidases or by Western blots.

Fabry disease patients with adverse reactions to the infusions are currently treated with antihistamines and antipyretics and the initial immune response has been manageable to date [61, 62], but it can be anticipated that life-long treatment required for these patients will lead to unacceptable levels of neutralizing antibodies. In this context it is reasonable to devise approaches to circumvent these adverse reactions and the development of derivatives of the enzyme with more activity per mg is a logical approach. Miyamura and coworkers [63] reported that carboxyl-terminal deletions of 2 to 10 amino acids of αGal led to an increase in activity of about 4 to 6-fold as compared to wild type (WT). However, this data was qualitative or semi-quantitative and relied on comparison of the amounts of mRNA present in Northern blots to αGal enzyme activity during transient infection of COS-1 cells. Here we use a *P. pastoris* expression system for the construction and purification of mutant enzymes with C-terminal deletions. The quantitative results reported here with purified enzymes reveal that C-terminal deletions results in an increase (Δ2, Δ4, Δ6, and Δ10) or decrease (Δ8) in enzyme activity.

Accordingly, there is a need for a method to purify recombinant α-Galactosidase A that provides high yield and maintains enzymatic activity.

SUMMARY OF THE INVENTION

In one embodiment, the invention provides a method of purifying recombinant alpha-galactosidase A. The method includes obtaining a lysate from cells recombinantly expressing alpha-galactosidase A grown in a cell culture medium having non-precipitating phosphate; contacting said lysate with a first chromatography media that binds α-D-mannopyranosyl or α-D-glucopyranosyl; eluting alpha-galactosidase A from the first chromatography media to generate a first eluate containing alpha-galactosidase A, wherein said eluting includes at least one elution pause between 4 and 16 hours; contacting the first eluate with a second chromatography media that binds galactose binding proteins; and eluting alpha-galactosidase A from said second chromatography media to generate a second eluate containing said recombinant alpha-galactosidase A.

In another embodiment, the invention provides a method of purifying recombinant human alpha-galactosidase A. The method includes obtaining a lysate from cells recombinantly expressing alpha-galactosidase A grown in a cell culture medium having non-precipitating sodium hexametaphosphate as a phosphate source; contacting the lysate with a first chromatography media includes Concanavalin A; eluting alpha-galactosidase A from said first chromatography media to generate a first eluate containing alpha-galactosidase A, wherein said eluting includes at least one elution pause of about 10-14 hours; contacting the first eluate with a second chromatography media, wherein the second chromatography media includes D-galactose; and eluting alpha-galactosidase A from said second chromatography media to generate a second eluate containing said recombinant human alpha-galactosidase A.

BRIEF DESCRIPTION OF THE DRAWINGS

FIG. 4A blot at shorter and FIG. 4B longer exposure.

[M+H]+ forms. Annotations in red and blue correspond to b-series and y-series ion fragments, respectively.

Figure 6A:
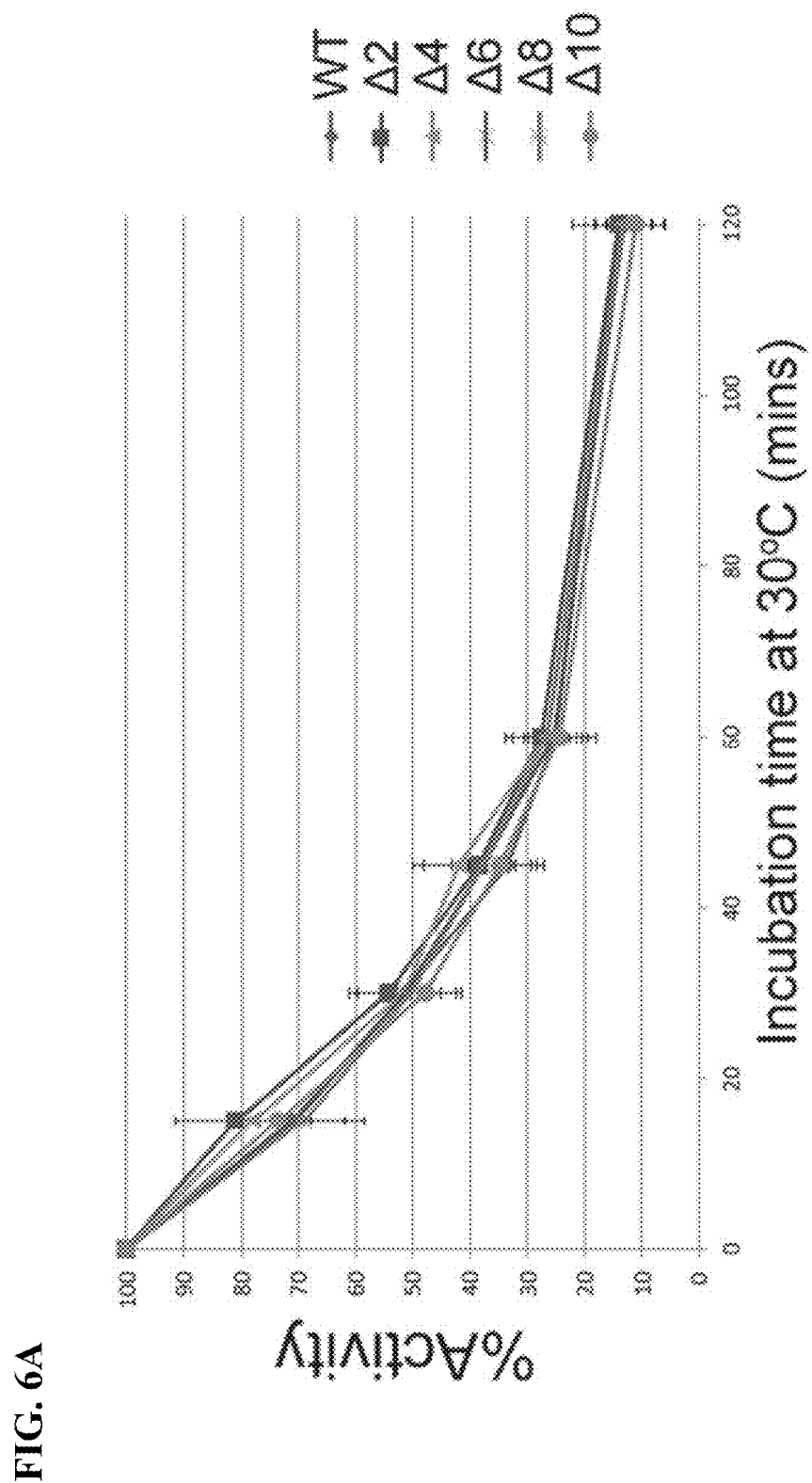
Figure 6B:
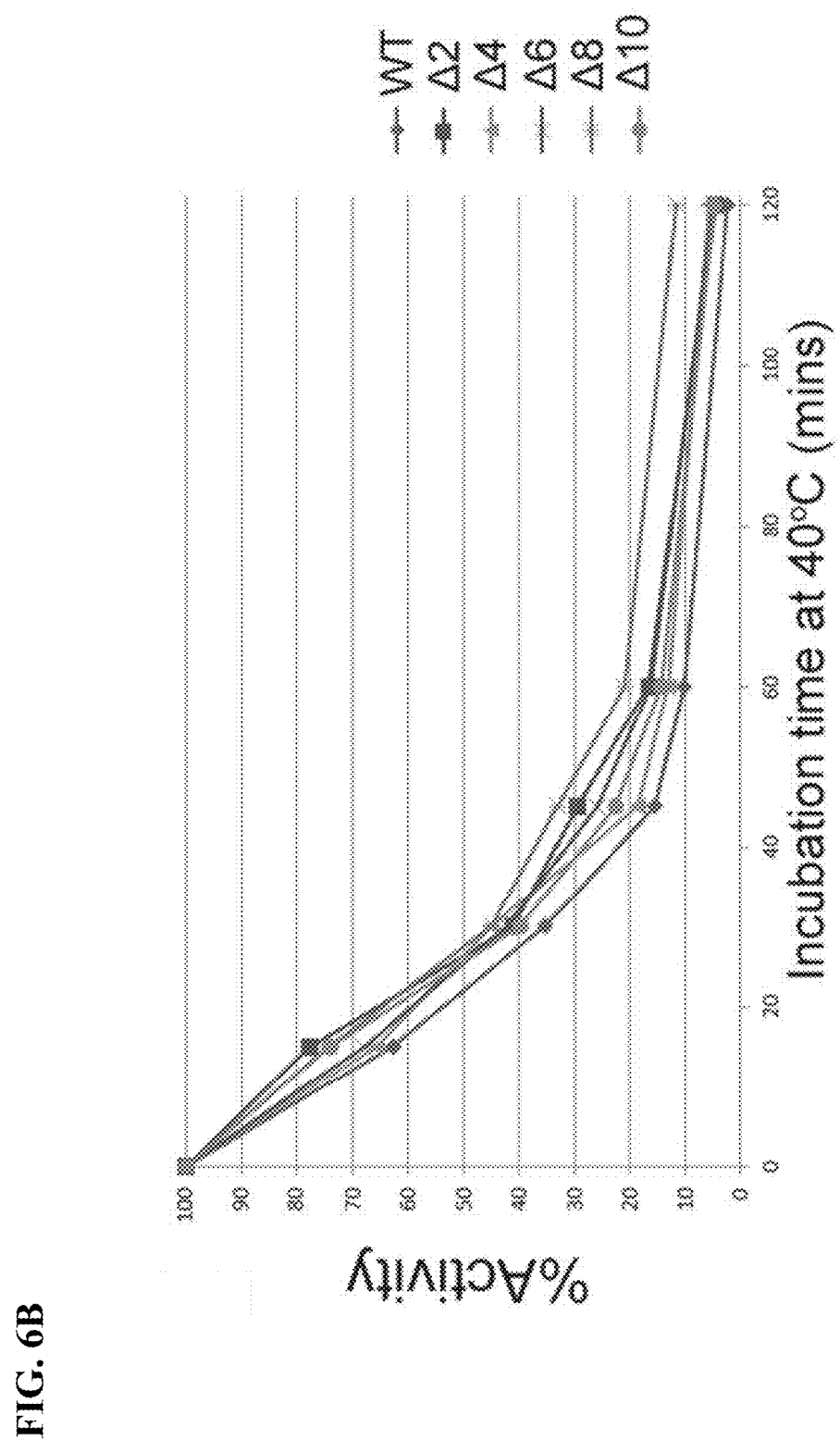
Figure 6C:
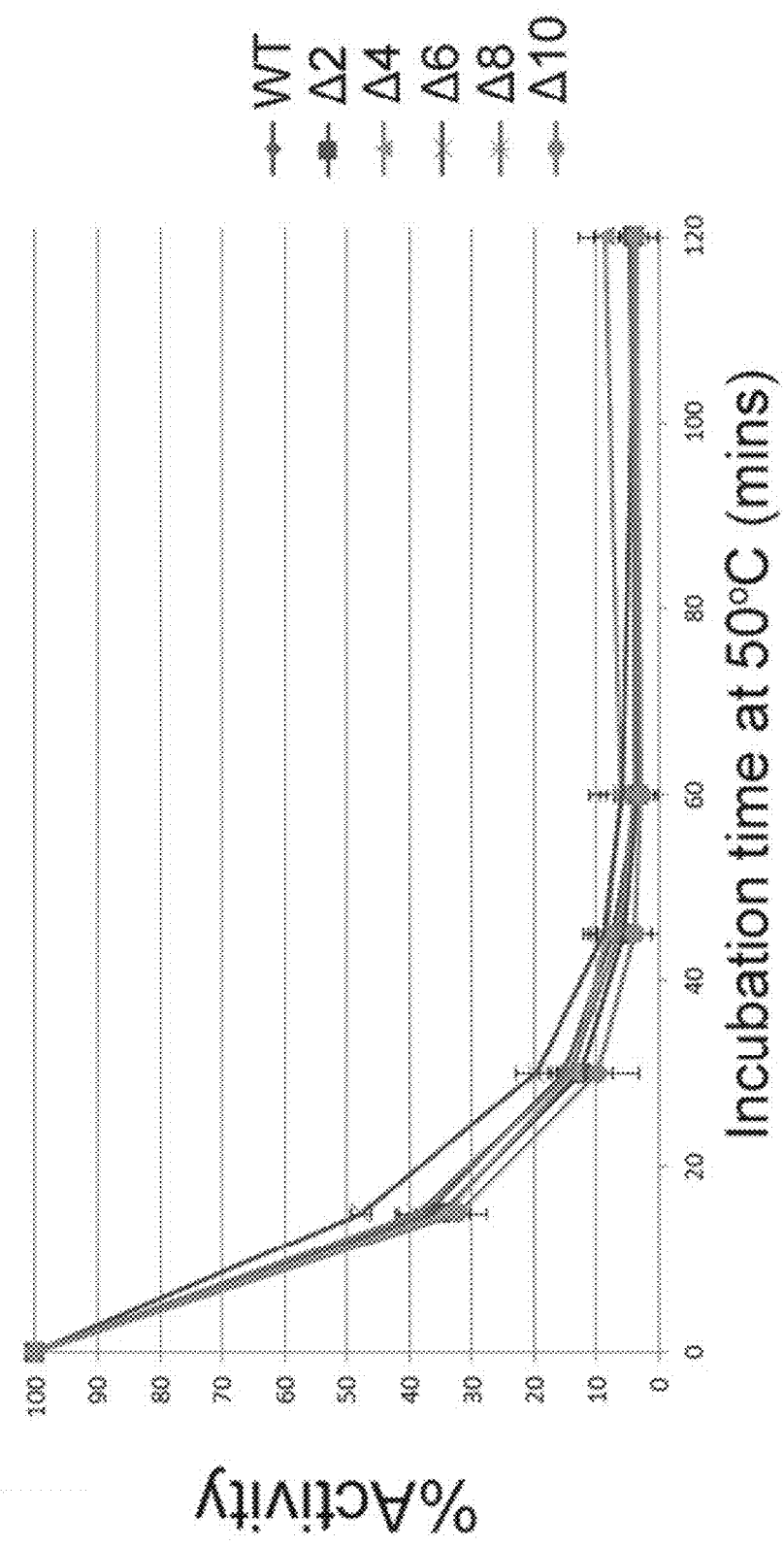

FIGS. 6A-B depict thermostability profiles of WT and mutant αGal. Stability of recombinant WT and Δ2 to Δ10 mutant αGal at 30° C. (FIG. 6A), 40° C. (FIG. 6B), and 50° C. (FIG. 6C) at pH 5.5 as monitored by fluorescent enzyme assay. Initial activities ranged from approximately 300 to 1,900 units/mL for all enzymes assayed. % Activity is normalized against activity at t=0 mins. Data points for (FIG. 6A) and (FIG. 6C) are the mean of a triplicate measurement with error bars equivalent to ±1 standard deviation. Data points for (FIG. 6B) are the results of a single measurement. MUG was used as the substrate for enzyme assay.

Figure 7:
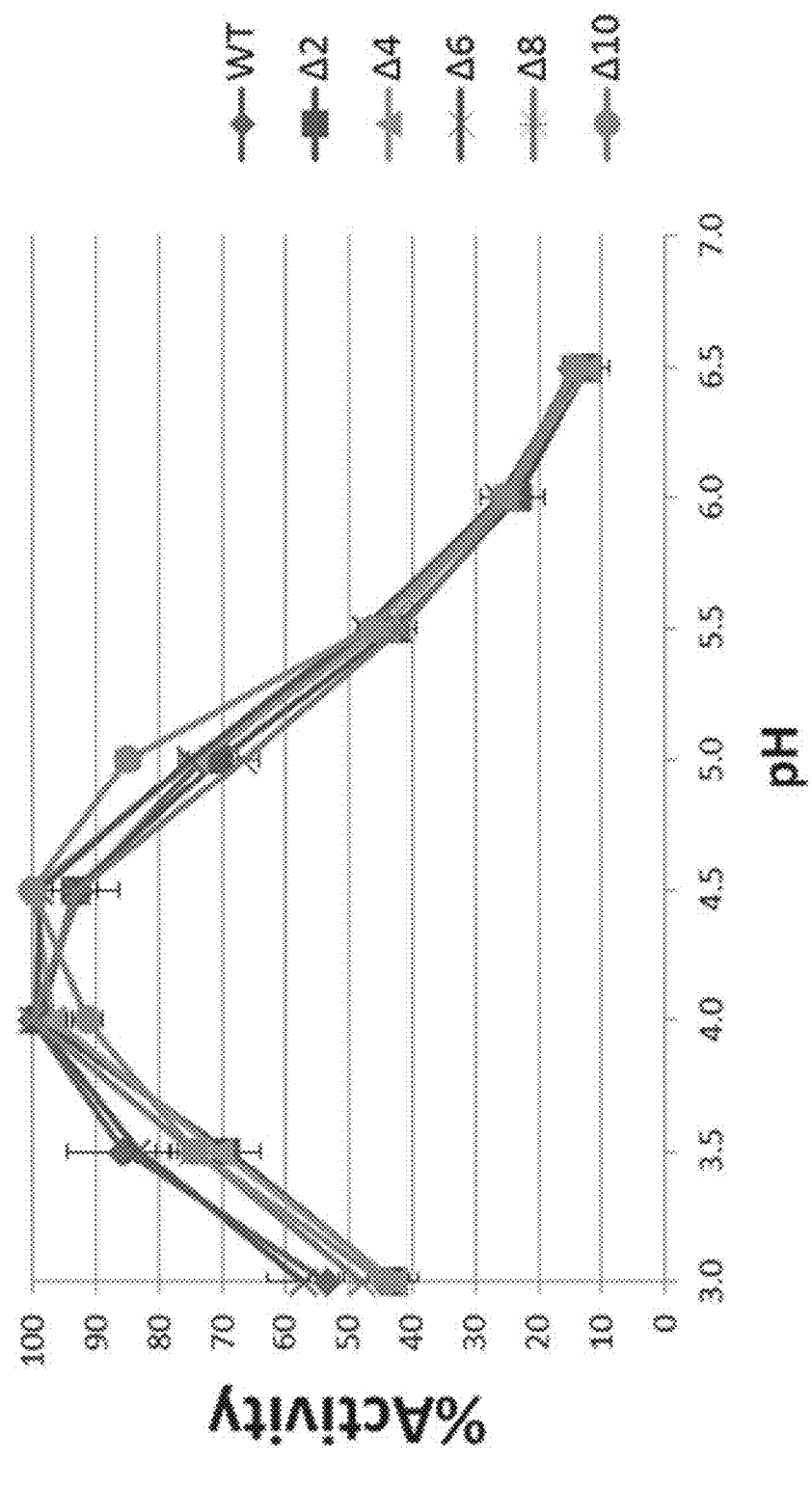

FIG. 7 depicts pH activity curves of WT and mutant αGal. pH activity curves for WT and Δ2 to Δ10 mutant αGal. % Activity is normalized against each enzyme's peak activity. Data points are the mean of a triplicate measurement and error bars are ±1 standard deviation. MUG was used as the substrate for enzyme assay.

Figure 8A:
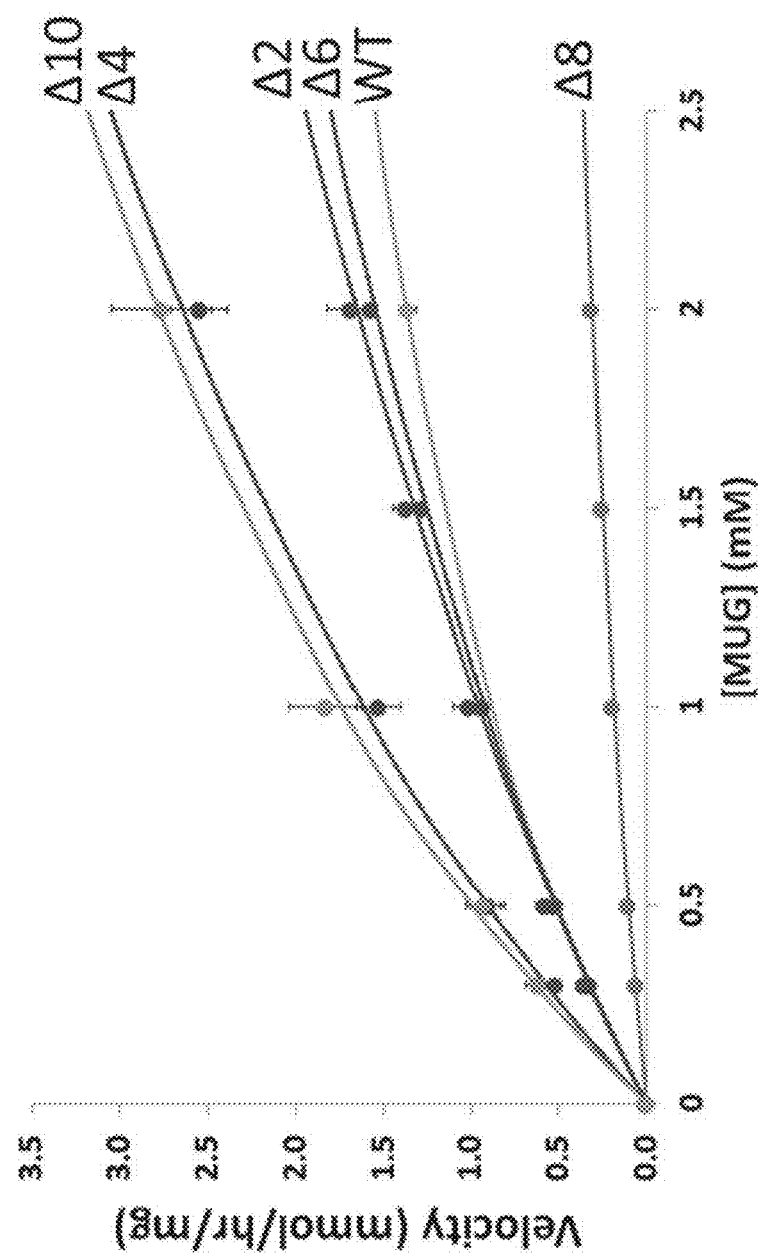
Figure 8B:
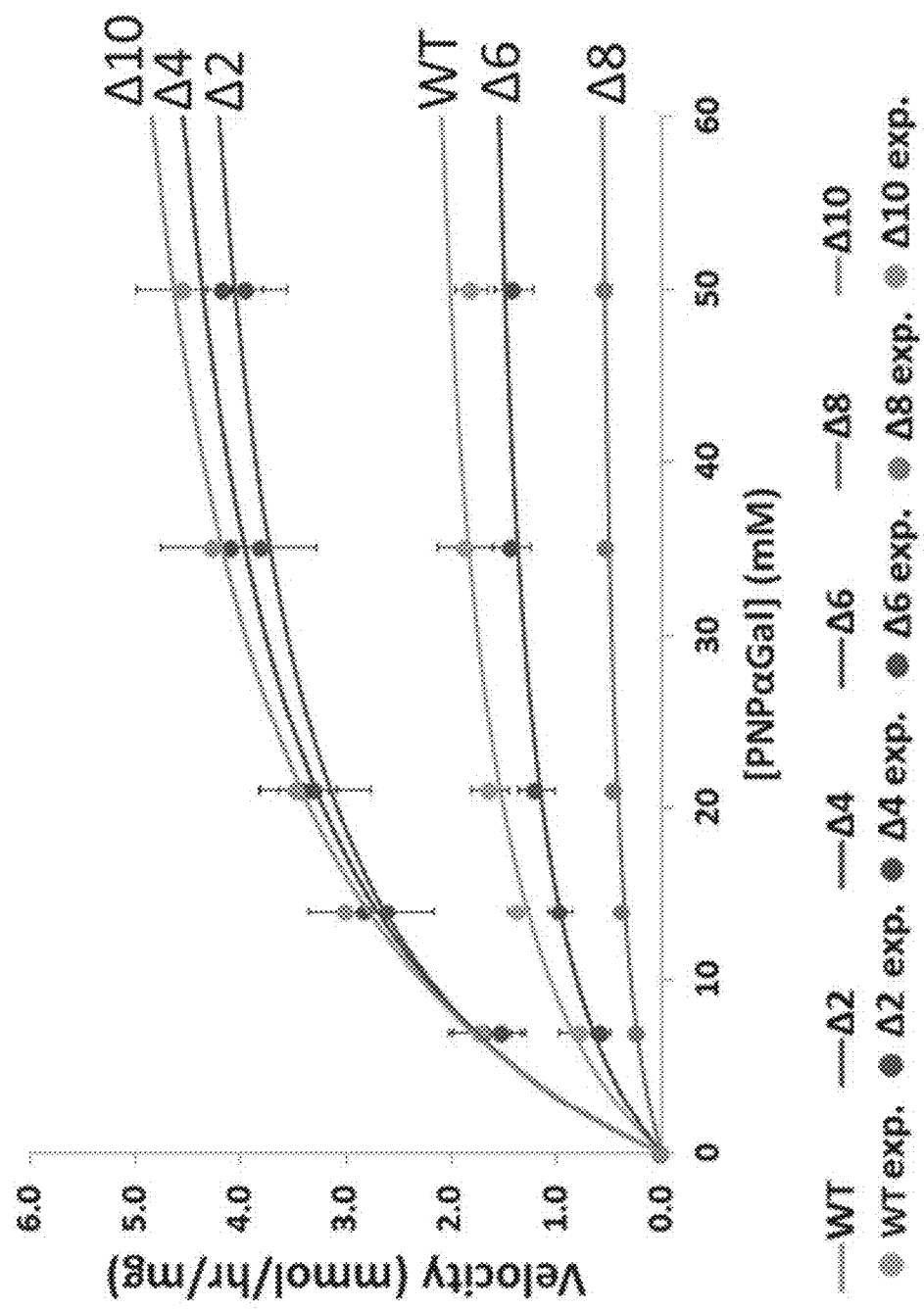

FIGS. 8A-B depict substrate saturation curves of WT and mutant αGal. Purified WT, Δ2, Δ4, Δ6, Δ8 and Δ10 αGal were enzyme assayed in 0.3 to 2.0 mM MUG (FIG. 8A) and in 7 mM to 50 mM PNPαGal (FIG. 8B) to measure initial velocities (mmol product per hr/mg enzyme). Km and Vmax parameters were extracted and compiled in Table 3. The figure indicates fits of Michaelis-Menten hyperbolas to experimental data indicated as mean±one standard deviation.

Figure 9B:
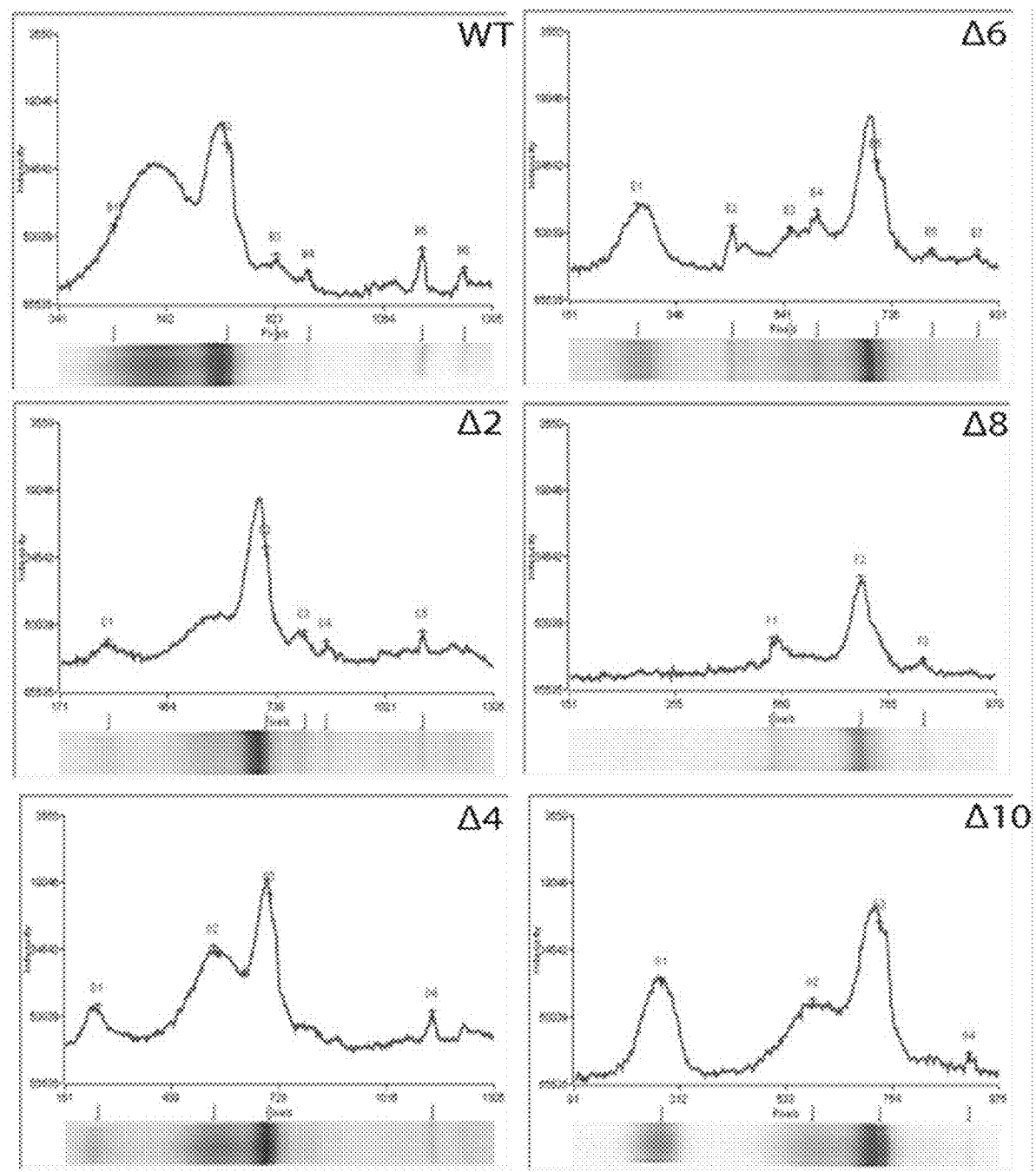

FIGS. 9A-B depict quantification of Bands in SDS-PAGE (FIG. 9A). Band intensities of the SDS-PAGE in (FIG. 3) were quantified by Image Acquisition and Analysis software (VisionWorks®LS, UVP Inc., Upland, Calif.) FIG. 9B.

Figures 10A, 10B:
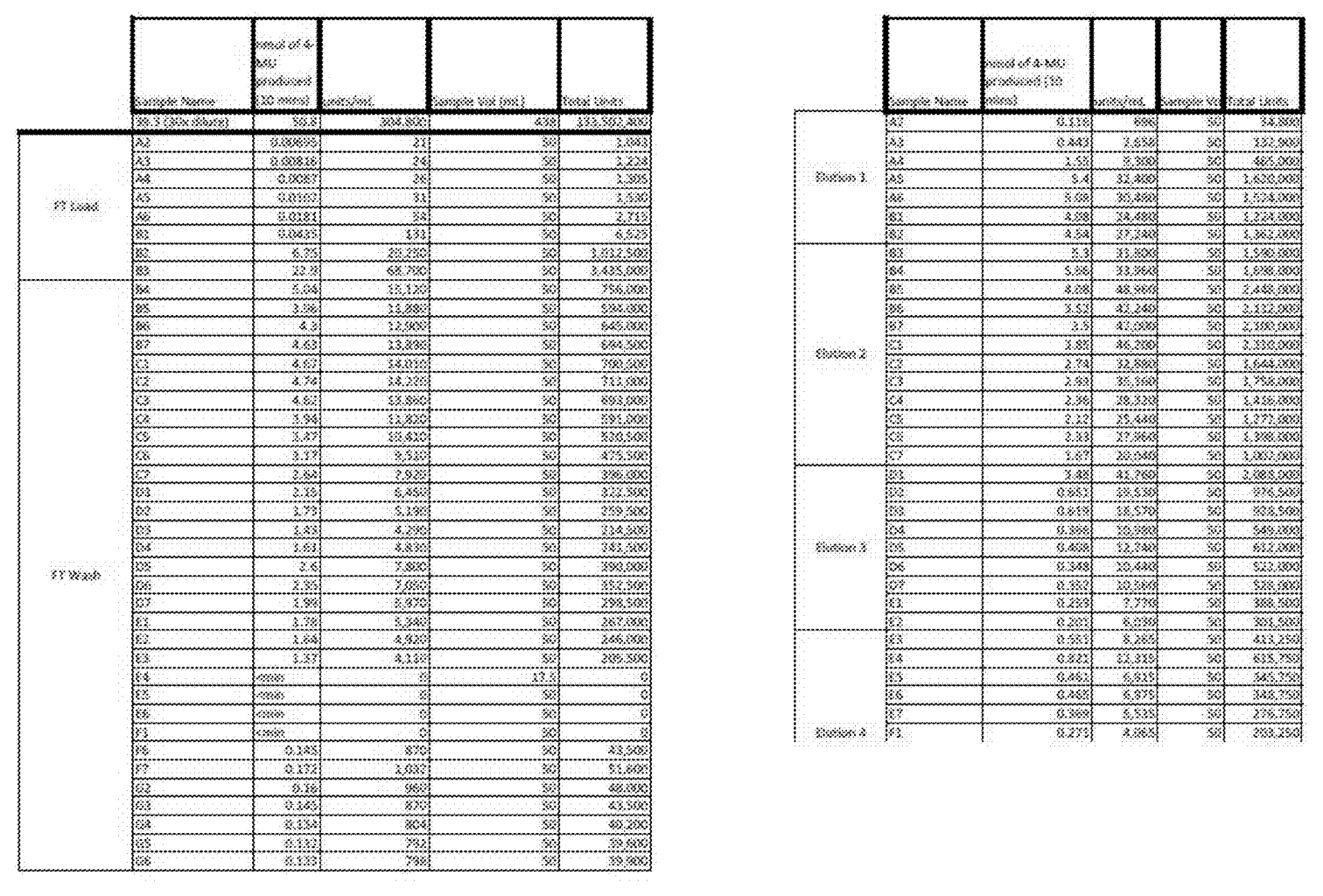
Figure 10C:
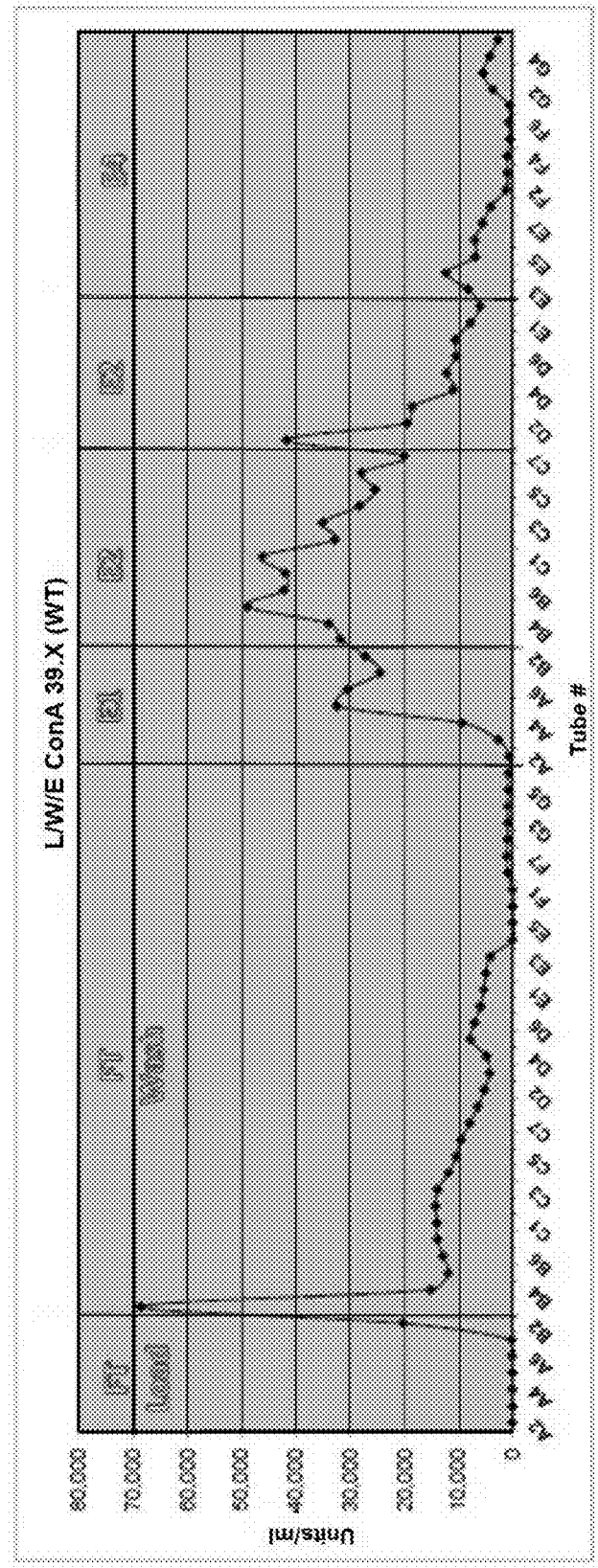

FIGS. 10A-C depict chromatogram (FIG. 10C) and fraction analysis (FIGS. 10A and 10B) of binding, washing, and elution sample through Concanavalin A(ConA) Sepharose 4B column.

Figure 11A:
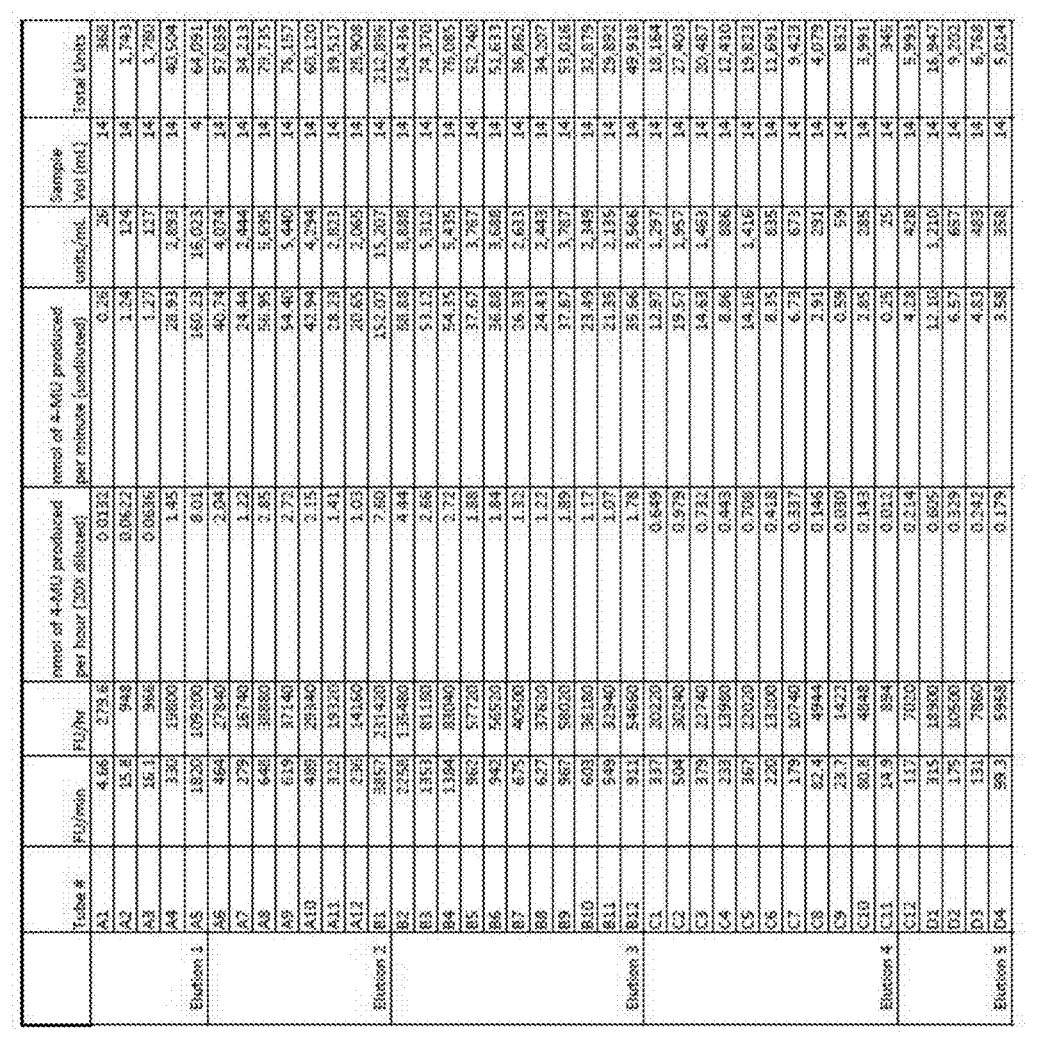
Figure 11B:
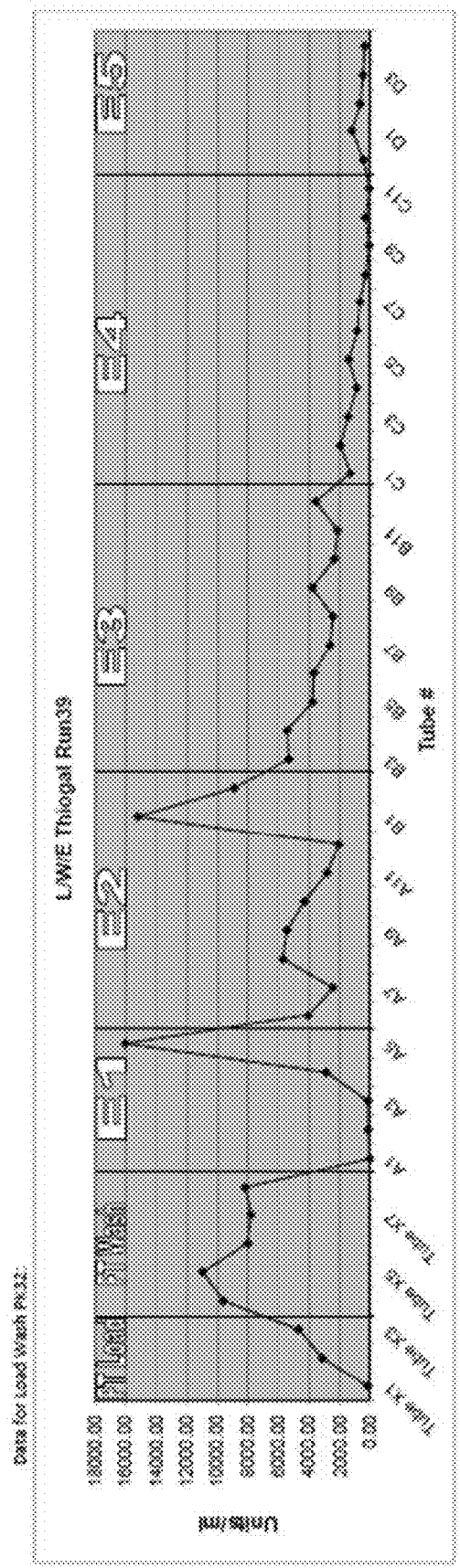

FIGS. 11A-B depict the chromatogram (FIG. 11B) and fraction analysis (FIG. 11A) of binding, washing, and elution of sample through a Thiogal column.

Figure 12:
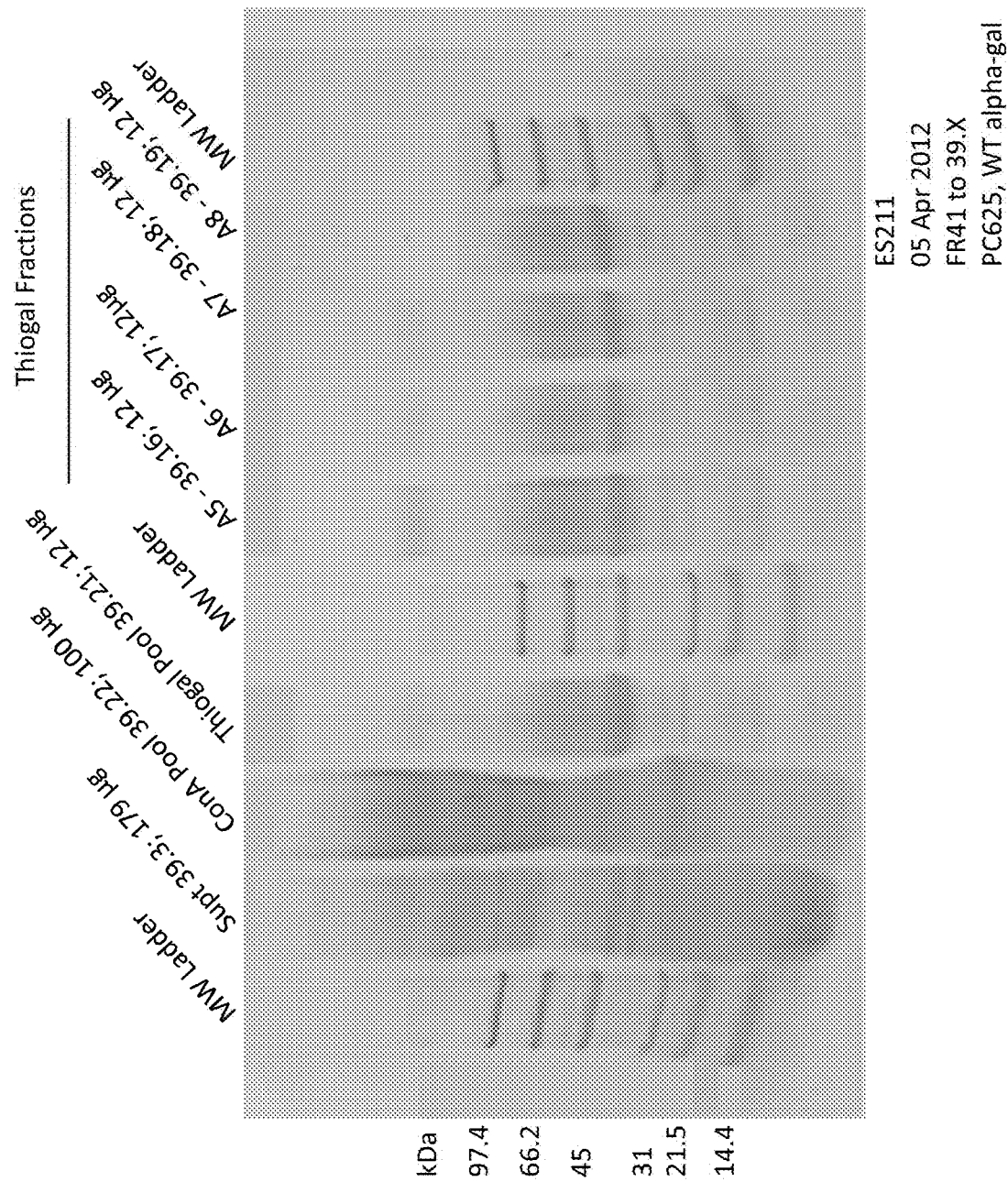

FIG. 12 depicts SDS-PAGE of sample fractions obtained from the preparation shown in FIGS. 10 and 11.

FIG. 13 depicts enzymatic activity of alpha-galactosidase A at different stages of purification.

DETAILED DESCRIPTION

The invention provides a method of purifying recombinant alpha-galactosidase A. The alpha-galactosidase A may be human alpha-galactosidase A, non-human alpha-galactosidase A, or a chimeric alpha-galactosidase A having similarity to human and non-human sequences. The recombinant alpha-galactosidase A may also have mutations that alter the catalytic activity. The recombinant alpha-galactosidase A may be full length or truncated. Examples of truncated alpha-galactosidase A include those having C-terminal truncations of 2, 4, 6, 8, 10, 12, or 14 amino acids.

A lysate is obtained from cells recombinantly expressing alpha-galactosidase A grown in a cell culture medium having non-precipitating phosphate. Any suitable cell capable of stably expressing alpha-galactosidase A may be used. An example of a suitable cell includes *Pichia pastoris*. Any suitable expression system capable of expressing alpha-galactosidase A may be used. Expression systems include plasmid borne expression systems or expression systems integrated within the genome. In some embodiments, non-precipitating sodium hexametaphosphate is the phosphate source for the culture medium. In other embodiments, phosphate glass may be used as the phosphate source. Sodium trimetaphosphate and/or sodium orthophosphate have also been contemplated as the phosphate source. The lysate may be generated by any known means. For example, cells recombinantly expressing alpha-galactosidase A may be harvested and the cells lysed by mechanical means or chemical means. An example of mechanical lysis includes sonication. The lysate may be clarified by at least one of centrifugation or filtration. Examples of filtration include passing the lysate through a 0.2 μm hollow fiber filter, and diafiltration across a 50 kDa pore size hollow fiber filter.

The lysate is then contacted with a first chromatography media to bind alpha-galactosidase A to the first chromatography media. As used herein, chromatography media may be in the form of a packed column or free-flowing slurry. The first chromatography media includes any media that binds α-D-mannopyranosyl, or α-D-glucopyranosyl. Examples of such media include Concanavalin A (ConA) immobilized on Sepharose™ 4B; and mannose-specific lectin from the snowdrop (*Galanthus nivalis*) bulb immobilized on a solid matrix. The first chromatography media may then be washed to remove any material non-specifically bound to it.

The alpha-galactosidase A bound to the first chromatography media is eluted by contacting the first chromatography media with an elution buffer to generate an eluate containing alpha-galactosidase A. Eluate, as used herein, is defined as elution buffer that has contacted the chromatography media and contains alpha-galactosidase A. This eluate is the first eluate. Any elution buffer capable of disrupting the binding of alpha-galactosidase A to the first chromatography media may be used. For example, the elution buffer may contain an increasing gradient (linear or step) of α-D-methylmannoside or α-D-methylglucoside. The use of glucose and mannose has also been contemplated. The elution buffer may also have a pH less than 6, less than 5, less than 4.5, or less than 4. The elution buffer contains non-near-saturating concentration of sugar.

Elution of alpha-galactosidase A from the first chromatography media may include at least one elution pause. An elution pause, as used herein, is defined as contacting elution buffer with the chromatography media, and pausing the flow of the elution buffer such that there is no flow across the chromatography media. By way of further explanation, the chromatography media is incubated with the elution buffer. In the case of column chromatography, for example, one or more column volumes of elution buffer are flowed through the chromatography column, and the flow is paused. In the case of batch chromatography, a defined volume of elution buffer is contacted with the media and maintained for an amount of time (pause). In one embodiment, the pause may be from 4-16 hours. In another embodiment, the pause is from 12-14 hours. In one embodiment, the flow is paused for at least 4 hours, preferably for at least 8 hours, and most preferably at least 12 hours.

The first eluate is contacted with a second chromatography media to bind alpha-galactosidase A to the second chromatography media. The first eluate may be subject to diafiltration, dialysis, or buffer exchange prior to contacting the second chromatography media. The second chromatography media is any media that binds galactose binding proteins. Examples of such media include D-galactose or C-type lectins. C-type lectin mutants engineered to have increased affinity for galactose have also been contemplated.

The alpha-galactosidase A is eluted from said second chromatography media by contacting it with a second elution buffer. Any elution buffer capable of disrupting the binding of alpha-galactosidase A to the second chromatography media may be used. The second elution buffer may contain an increasing gradient (linear or step) of D-galactose. The elution buffer may also have a pH less than 6, less than 5, less than 4.5, or less than 4.

In the specification, numerous specific details are set forth in order to provide a thorough understanding of the present embodiments. It will be apparent, however, to one having ordinary skill in the art that the specific detail need not be employed to practice the present embodiments. In other instances, well-known materials or methods have not been described in detail in order to avoid obscuring the present embodiments.

Throughout this specification, quantities are defined by ranges, and by lower and upper boundaries of ranges. Each lower boundary can be combined with each upper boundary to define a range. The lower and upper boundaries should each be taken as a separate element.

Reference throughout this specification to "one embodiment," "an embodiment," "one example," or "an example" means that a particular feature, structure or characteristic described in connection with the embodiment or example is included in at least one embodiment of the present embodiments. Thus, appearances of the phrases "in one embodiment," "in an embodiment," "one example," or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

As used herein, the terms "comprises," "comprising," "includes," "including," "has," "having," or any other variation thereof, are intended to cover a non-exclusive inclusion. For example, a process, article, or apparatus that comprises a list of elements is not necessarily limited to only those elements but may include other elements not expressly listed or inherent to such process, article, or apparatus.

Further, unless expressly stated to the contrary, "or" refers to an inclusive "or" and not to an exclusive "or". For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of any term or terms with which they are utilized. Instead, these examples or illustrations are to be regarded as being described with respect to one particular embodiment and as being illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example," "for instance," "e.g.," and "in one embodiment."

In this specification, groups of various parameters containing multiple members are described. Within a group of parameters, each member may be combined with any one or more of the other members to make additional sub-groups. For example, if the members of a group are a, b, c, d, and e, additional sub-groups specifically contemplated include any one, two, three, or four of the members, e.g., a and c; a, d, and e; b, c, d, and e; etc.

EXAMPLES

The present invention is illustrated in further details by the following non-limiting examples.

Example 1. Materials and Methods

Cell Strains and Plasmids

The *P. pastoris* host strain X-33 (No. K1740-01), *E. coli* strains TOP10 (No. C4040-50) and TOP10F' (No. C665-11), plasmid pPICZαA (No. K1740-01), and TOPO® XL PCR cloning kit (No. K4700-10) were purchased from Invitrogen.

TABLE 1

Table 1. Strains and Plasmids.

| Strain | Species | Plasmid | Description |
|---|---|---|---|
| CC878 | E. coli | pCC248 | pCR-XL-TOPO derivative plasmid a modified cDNA using primers AAF and AARD4 to generate C-terminal deletion of 4 amino acids (Δ4) |
| CC892 | E. coli | pCC262 | pPICZαA derivative plasmid with Δ4 CDNA insert |
| CC970 | E. coli | pCC278 | pCR-XL-TOPO derivative plasmid a modified cDNA using primers AAF and AARD6 to generate C-terminal deletion of 6 amino acids (Δ6) |
| CC973 | E. coli | pCC281 | pCR-XL-TOPO derivative plasmid a modified cDNA using primers AAF and AARD10 to generate C-terminal deletion of 10 amino acids (Δ10) |
| CC983 | E. coli | pCC291 | pPICZαA derivative plasmid with Δ6 CDNA insert |
| CC990 | E. coli | pCC298 | pPICZαA derivative plasmid with Δ10 CDNA insert |
| CC993 | E. coli | pCC301 | pCR-XL-TOPO derivative plasmid a modified cDNA using primers AAF and AARD2 to generate C-terminal deletion of 2 amino acids (Δ2) |
| CC994 | E. coli | pCC302 | pCR-XL-TOPO derivative plasmid a modified cDNA using primers AAF and AARD8 to generate C-terminal deletion of 8 amino acids (Δ8) |
| CC995 | E. coli | pCC303 | pPICZαA derivative plasmid with Δ2 cDNA insert |
| CC997 | E. coli | pCC305 | pPICZαA derivative plasmid with Δ8 cDNA insert |
| PC626 | P. pastoris | pCC106 | Integrated pPICZαA derivative with WT cDNA insert [53] |
| PC897 | P. pastoris | pCC262 | Integrated pPICZαA derivative with Δ4 cDNA insert |
| PC958 | P. pastoris | pCC291 | Integrated pPICZαA derivative with Δ6 cDNA insert |
| PC960 | P. pastoris | pCC298 | Integrated pPICZαA derivative with Δ10 cDNA insert |
| PC971 | P. pastoris | pCC303 | Integrated pPICZαA derivative with Δ2 cDNA insert |
| PC973 | P. pastoris | pCC305 | Integrated pPICZαA derivative with Δ8 cDNA insert |

TABLE 1-continued

Table 1. Strains and Plasmids.

| Strain | Species | Plasmid | Description |
|---|---|---|---|
| TOP10 | E. coli | None | E. coli host for modified Δ2, Δ6, Δ8, Δ10 cDNA plasmids |
| TOP10F' | E. coli | None | E. coli host for pCC106 and modified Δ4 cDNA plasmid |
| X-33 | P. pastoris | None | Expression host for αGal expression |

Doi: 10.1371/journal.pone.0118341.t001

TABLE 2

Primers Used for DNA Sequence Analysis.

| Primer | Sequence | Function |
|---|---|---|
| 5' AOX | 5' GACTGGTTCCAATTGACAAGC 3' (SEQ ID NO: 1) | DNA sequencing primer for pPICZαA |
| 3' AOX | 5' GCAAATGGCATTCTGACATCC 3' (SEQ ID NO: 2) | DNA sequencing primer for pPICZαA |
| α-factor | 5' TACTATTGCCAGCATTGCTGC 3' (SEQ ID NO: 3) | DNA sequencing primer for pPICZαA |
| M13: forward | 5' GTAAAACGACGGCCAG 3' (SEQ ID NO: 4) | DNA sequencing primer for pCR-XL-TOPO |
| M13: reverse | 5' CAGGAAACAGCTATGAC 3' (SEQ ID NO: 5) | DNA sequencing primer for pCR-XL-TOPO |

Note.
Primers were HPLC purified, 50 nmoles from Invitrogen
Doi:10.1371/journal.pone.0118341.t002

Bioreactor Expression of Recombinant αGal in *P. pastoris*

High-cell-density fermentation was carried out as previously described [53] with a modified growth medium utilizing non-precipitating sodium hexametaphosphate as a phosphate source [64] and modified for a 7 L Applikon bioreactor. Fermentation medium of 3.5 L (0.93 g/l CaSO4, 18.2 g/l K2SO4, 14.9 g/l MgSO4.7 H2O, 9 g/l (NH4)2SO4, 40.0 g/l glycerol) was autoclaved at 121° C. for 20 min in the vessel. After cooling to room temperature, filter sterilized sodium hexametaphosphate (25 g/l of fermentation basal salt medium dissolved in 500 ml of deionized water) and 0.435% PTM1 trace elements (CuSO4.5 H2O 6.0 g, NaI 0.08 g, MgSO4.H2O 3.0 g, Na2MoO4.2 H2O 0.2 g, H3BO3 0.02 g, CoCl2 0.5 g, ZnCl2 20.0 g, FeSO4.7 H2O 65.0 g, biotin 0.2 g, 5.0 ml H2SO4 per liter) were added to complete the fermentation medium. The pH was adjusted to 6.0 using ammonium hydroxide (28%).

Four frozen MGY cultures of 4 ml each were used to inoculate four 100 ml MGY cultures in 1-liter baffled flasks and grown at 250 rpm and 30° C. until the OD600 reached 2 to 6. The cultivation was divided into three phases, the glycerol batch, glycerol-fed batch, and methanol-fed batch. The glycerol batch phase was initiated with 400 ml of inoculum shake-flask culture added to 4 L of the fermentation medium containing 4% glycerol and an initial value of 100% dissolved oxygen until a spike was observed indicating complete consumption of glycerol. Next, the glycerol-fed batch phase was initiated and a 50% w/v glycerol feed rate of 18.15 ml/h/liter initial fermentation volume and maintained until a cell yield of 180 to 220 g/liter wet cells was achieved. At this point the glycerol feed was terminated manually and a methanol-fed batch phase was initiated by starting a 100% methanol feed containing 12 ml PTM1 trace salts per liter. Methanol was initially fed at 3.6 ml/h/liter of initial fermentation volume, then increased to 7.3 ml/h/liter and finally increased to 10.9 ml/h/liter of initial fermentation volume for the remainder of the fermentation. Dissolved oxygen spikes were used during the glycerol-fed batch phase and methanol-fed batch phase and to monitor substrate levels. A dissolved oxygen level of 40%, pH of 6, and temperature of 25° C. were maintained by an ADI 1030 regulator. Sampling was performed at the end of each phase and at least twice daily and analyzed for cell wet weight and increased αGal activity over time. Cultivation was terminated once a plateau in αGal activity was observed.

Construction of Strains

Figure 1:
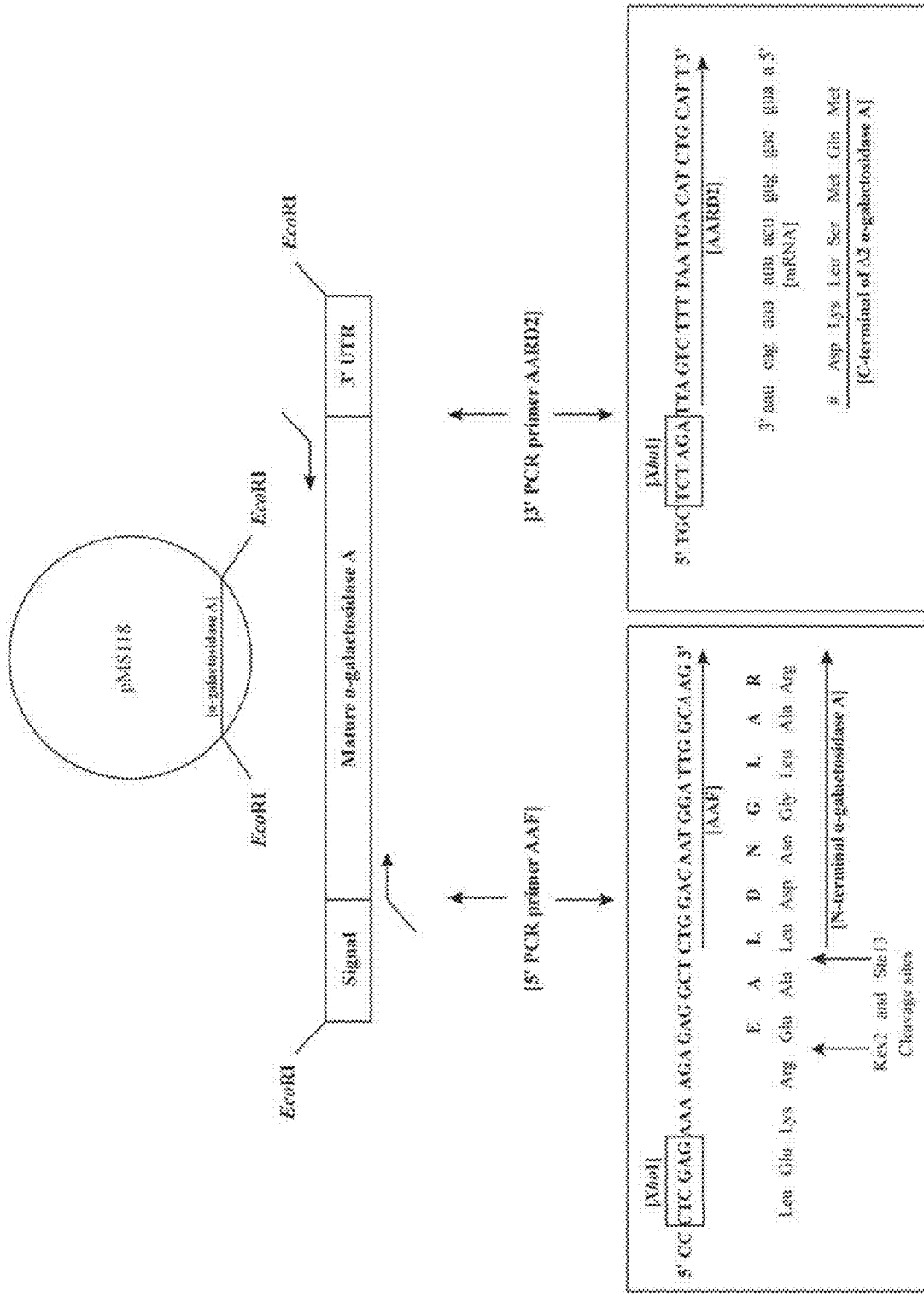
FIG. 1 depicts introduction of a C-terminal deletion of 2 amino acids into αGal. The strategy shown here for the Δ2 mutant was used to generate all five deletion mutations (FIG. 2). Plasmid pMS118 [48] contains the αGal cDNA cloned as an EcoRI fragment to the EcoRI site of plasmid pUC9. Primers AAF and AARD2 (FIG. 2) were used as PCR primers for plasmid pMS118 DNA to generate cDNAs with a 50 extension containing an XhoI site, Kex2 and Ste13 yeast signal cleavage sites, a 30 end with an introduced XbaI site, and a deletion of C-terminal amino acids to generate the Δ2 mutant. Primer AAF anneals to the cDNA at the sequences encoding the N-terminal sequences of αGal and primer AARD2 anneals to the C-terminal sequences of αGal. Primer AARD2 anneals 12 nucleotides from the 30 end of the cDNA and introduces a stop codon (UAA) after the aspartate codon three amino acids from the C-terminal end of the coding sequences of αGal resulting in a deletion of the two C-terminal amino acids (Leu-Leu) of the human enzyme (right panel). Cloning to the XhoI and XbaI sites of plasmid pPICZαA generates a protein fusion with the yeast signal peptide coding sequences in the vector. This signal peptide is removed by the Kex2 and Ste13 yeast signal peptidases through cleavage immediately upstream of the leucine, corresponding the first amino acid of the mature form of αGal (left panel). This strategy was generalized to create the other deletion mutants using the primers in FIG. 2. In the left panel, the N-terminal peptide LDNGLAR was identified in mass spectrometric analysis while EALDNGLAR was not (FIG. 5).

Plasmid pMS118 [48] contains the αGal cDNA cloned as an EcoRI fragment to the EcoRI site of plasmid pUC9. PCR primers (FIG. 1, 2) were used with plasmid pMS118 DNA and the PCR system (Roche, No. 11732641001) according to the vendor's instructions. This generated cDNAs with a 5' extension containing an XhoI site, Kex2 and Ste13 yeast signal cleavage sites, a 3' end with an XbaI site, and a deletion of C-terminal amino acids to generate Δ2 to Δ10 mutants (FIG. 1, 2). The PCR products were ligated to pCR-XL-TOPO to generate Δ2 to Δ10 plasmids (Table 1). These plasmids were used for electroporation [53] into *E. coli* strain TOP10 or TOP10F' (Table 1).

Purification of αGal Using Double Affinity Chromatography

Purification was as described [53, 65] with minor modifications (below). Bioreactor supernatant was passed through a 0.2 μm hollow fiber filter (Spectrum Labs, No. M22M-300-01N) and subjected to diafiltration using a 50 kDa pore size hollow fiber filter (Spectrum Labs, No. M25S-300-01N) against wash buffer (0.1 M sodium acetate buffer, pH 6.0, 0.1 M NaCl, 1 mM MgCl2, 1 mM CaCl2, 1 mM MnCl2). The resulting supernatant was applied to a Con A Sepharose 4B (GE Healthcare No. 17-0440-01) column, pre-equilibrated with wash buffer, and washed with 5 column volumes of wash buffer. It was observed that near-saturating sugar eluent concentrations do not improve glycoprotein recovery as compared to lower concentrations and that elution phase pauses improve recovery [66]. In accordance with these findings, elution of αGal was carried out using modified elution buffer I (0.5 M methyl-α-D-mannopyranoside, 0.25 M methyl-α-D-glucopyranoside in wash buffer) over 1.5 column volume blocks separated by 12-hour interval soaks. Elution was discontinued when the absorbance at 280 nm and enzyme assays showed negligible presence of protein and αGal activity. No substantial difference in recovered enzyme was observed between purifications carried out with modified elution buffer I versus sugar saturated elution buffer I (data not shown). The Con A pool was subjected to diafiltration using a 50 kDa pore size hollow fiber filter (Spectrum Labs, No. M25S-300-01N) against binding buffer (25 mM citrate-phosphate buffer, pH 4.8 containing 0.1 M NaCl).

The Con A pool was applied to an immobilized-D-galactose gel column (Thio-Gal, Pierce No. 20372) pre-equilibrated with binding buffer. The column was washed with 5 column volumes of binding buffer and αGal was eluted with elution buffer II (25 mM citrate-phosphate buffer, pH 5.5, 0.1M NaCl, 0.1MD-galactose) over 1.5 column volume blocks separated by 12 hour soaks. Fractions were assayed for enzyme activity and protein concentration and a peak tube with high specific activity was chosen as the sample to be used in a substrate saturation curve.

Electrophoresis Analysis

Samples (8 μg) were mixed with an equal volume of reducing sample buffer (Bio-Rad Laemmli sample buffer with 5% β-mercaptoethanol) and heated for 5 minutes at 95° C. before loading on a Mini-Protean TGX Precast Gel 4-20% (w/v) (Bio-Rad No. 456-1094). Bands were visualized by Coomassie blue staining via the modified Fairbanks protocol [67].

Western Blot Analysis

Western blot analysis was performed using an anti-αGal polyclonal antibody produced in chicken (Pierce/ThermoSci #PA1-9528) and horseradish peroxidase-conjugated anti-Chicken IgY antibody (Sigma #A9046). After SDS-PAGE (2 μg of samples loaded), the gel was incubated with a nitrocellulose membrane (Whatman, No. 10402594) for 15 minutes at room temperature in Transfer Buffer (48 mM Tris, 39 mM glycine, 20% MeOH, pH 9.2) and the proteins were then transferred to the nitrocellulose membrane using a Bio-Rad Trans Blot SD Semi-Dry Transfer Cell. The membrane was blocked with 8% (w/v) non-fat dried milk in PBST [10 mM Na2HPO4, 1.8 mM KH2PO4, 137 mM NaCl, 2.7 mM KCl and 0.2% Tween 20 (pH 7.4)] at room temperature for 20 minutes. The membrane was then treated with primary antibody diluted in a milk/blot solution [1% (w/v) non-fat dried PBST] for 2 h at room temperature with mild shaking. After rinsing with PBST solution, the membrane was treated for 1 h at room temperature with secondary antibody diluted in the milk/blot solution. Protein bands were visualized on Kodak BioMax XAR film (VWR #1B1651454) with a Konica SRX-101A processor.

Enzyme and Protein Assays

Activity of αGal was assayed using the synthetic substrate, 4-methylumbelliferyl-α-D-galactopyranoside (MUG) as described [53] with modifications to a microtiter plate format (below).

Enzyme activity is measured in units/ml where one unit is defined as the amount of enzyme required to convert 1 nmole of MUG to 4-methylumbelliferone in one hour at 37° C. An aliquot of 3 μl was added to 27 μl of enzyme assay buffer (5 mM MUG in 40 mM sodium acetate buffer, pH 4.5). This mixture was incubated at 37° C. and 10 μl aliquots were taken at two time points and added to 290 μl of 0.1M diethylamine in a microtiter plate to stop the reaction. Typically time points were chosen as 1-4 minutes and values that were proportional to time were considered valid. The fluorescence of each sample was measured at an excitation wavelength of 365 nm and an emission wavelength of 450 nm using a Tecan Infinite F200 microtiter plate reader. A standard curve of 10 μl of 0-0.5 nmol 4-methylumbelliferone dissolved in MeOH in 290 μl of 0.1 Mdiethylamine was used to quantitate MUG cleavage at specific time intervals. Analysis of the effects of MeOH indicated no effect on the 4-methylumbelliferone standard curve.

For samples containing higher protein concentrations, the BioRad DC Protein Assay (No. 500-0116) with a standard curve of (0.2-1.5) mg/ml was used according to the manufacturer's specifications. For dilute samples of purified αGal, a more sensitive fluorescence-based fluorescamine assay [68] with a standard curve containing lower protein concentrations of (4.0-160) μg/ml was used. Briefly, 150 μl of 0.05 Msodium phosphate buffer and 50 μl of 1.08 mM fluorescamine dissolved in acetone were added to an aliquot of 50 μl of the sample and standards, mixed and incubated for 12 minutes. The fluorescence of each sample was measured at an excitation wavelength of 400 nm and an emission wavelength of 460 nm. Bovine serum albumin (Bio-Rad No. 500-0112) was used as the standard in both assays. Absorbance and fluorescence measurements were conducted on a Tecan Infinite F200 microplate reader using 96-well plates.

Mass Spectrometry of a Purified Mutant Enzyme

The Δ6 mutant was selected for mass spectrometry analysis conducted at the Rockefeller University Proteomics Resource Center in collaboration with M. T. Mark. SDS-PAGE gel slices were washed, de-stained, reduced using 10 mM dithiothreitol, alkylated using 100 mM iodoacetamide, and digested using trypsin. Peptides were then extracted from the gel two times, dried, and re-suspended in a 5% acetonitrile and 2% formic acid mixture. One third of each sample was loaded onto a C18 PepMap1000 micro-precolumn (300 μm I.D., 5 mm length, 5 μm beads, Thermo Scientific) at a flow-rate of 5 μl/min, and subsequently onto an analytical C18 column (75 μm I.D., 3 μm beads, Nikkyo Technos Co.) at a flow rate of 300 nl/min. The gradient was 40 min long in the range 5 to 45% B (buffer A was 0.1% formic acid in water, and buffer B was 0.1% formic acid in acetonitrile). Eluted peptides were applied by electrospray directly into the LTQ-Orbitrap XL mass spectrometer from Thermo Scientific, operating in a 300 to 1800 m/z mass range. Tandem mass spectrometry was performed by collision induced dissociation using nitrogen as a collision gas. The resulting spectra were analyzed using Mascot and Proteome Discoverer 1.3 (Thermo Scientific) to identify the peptides in the sample.

Thermostability and pH Optimum of WT and Mutant αGal

Purified enzyme samples were diluted in 25 mM citrate-phosphate buffer, pH 5.5, 0.1 MNaCl, 0.01 MD-galactose. Samples of 50 μl were incubated in triplicate at 50° C., 30° C. and 40° C. Aliquots of 3 μl were removed for enzyme assays every 15 minutes for two hours. Samples were assayed in 0.02 M citrate buffer, pH 3.0-pH 6.5, containing 2 mM MUG.

Characterization of Kinetic Properties

Substrate saturation curves for αGal have been reported using MUG at concentrations up to 2 mM, 5 mM, and 10 mM (in the presence of 0.1% BSA and 0.67% EtOH [24]). We noted that under our experimental conditions MUG is fully soluble at 2 mM, partially soluble at 5 mM, and chemically oversaturated at higher concentrations. Other investigators reported the use of sonication or detergent treatment to increase the solubility of MUG (e.g., [69]) but we avoided this approach in order to avoid potential artifacts due to the use of these techniques. Substrate saturation curves using 2 mM and 5 mM MUG as the highest concentrations were carried out and the kinetic parameters for αGal were calculated separately obtaining similar values. The values reported here (Table 3a) were obtained using a substrate saturation curve of 0.3 to 2 mM MUG since this is the highest concentration that is fully soluble under our experimental conditions. The Km and Vmax values were calculated using Lineweaver-Burk and non-linear regression through the program Sigma-Plot (Systat Software, San Jose, Calif.).

Kinetic parameters were also determined using the colorimetric substrate, para-nitrophenyl-α-D-galactopyranoside (PNPαGal) [70]. Purified enzymes were diluted to approximately 20,000 units/mL as determined by fluorescent MUG assay. These diluted samples were then added at a proportion of 1:9 citrate-phosphate buffer (0.1 M) containing 7-50 mM PNPαGal. Aliquots of 20 μl of the enzymatic reaction were removed at 15 minute intervals to terminate the reaction over the course of an hour and added to 320 μl of borate buffer (pH 9.8) in a microplate [71]. Product formation was monitored by absorbance at 400 nm. Linear reaction velocities were observed for all measurements. A standard curve of 0-150 μMp-nitrophenylate in borate buffer (pH 9.8) [71] was used to quantitate product formation. Km and Vmax parameters were determined through non-linear regression using Sigma-Plot (Systat Software, San Jose, Calif.).

Protein Structure Analysis

The crystal structure of αGal (PDB 1R47) was viewed and analyzed in PyMOL (Delano Scientific). The MSLDKLL and QMSLKDLL peptides corresponding to the last 7 or 8 C-terminal amino acids of αGal were built in PyRosetta [72] and visualized in PyMOL [73]. Interatomic distances were measured using the PyMOL wizard distance command.

A homology model of the coffee bean α-galactosidase was generated on the Phyre2 server[74]. The primary sequence of coffee bean α-galactosidase (GenBank No. AAA33022.1) was set as the query. The crystal structure of rice α-galactosidase (73% sequence identity to coffee α-galactosidase, PDB#1UAS) was set as the template. Superposition of the coffee homolog and human crystal structure of αGal (PDB#1R47) was conducted in PyMOL [73]. Primary sequence alignments were carried out in ClustalOmega (EMBL-EBI).

Example 2. Purification of WT and Mutant αGal

The WT and mutant enzymes were obtained from a 7 L bioreactor and purified (Table 4, FIG. 3) using Con A and Thio-Gal tandem affinity chromatography. This two column purification is simpler and faster than our previous purification methods that used three [50] or four [49, 53]columns and the yield, degree of purity, and final specific activities were similar for all three methods.

Figure 3:
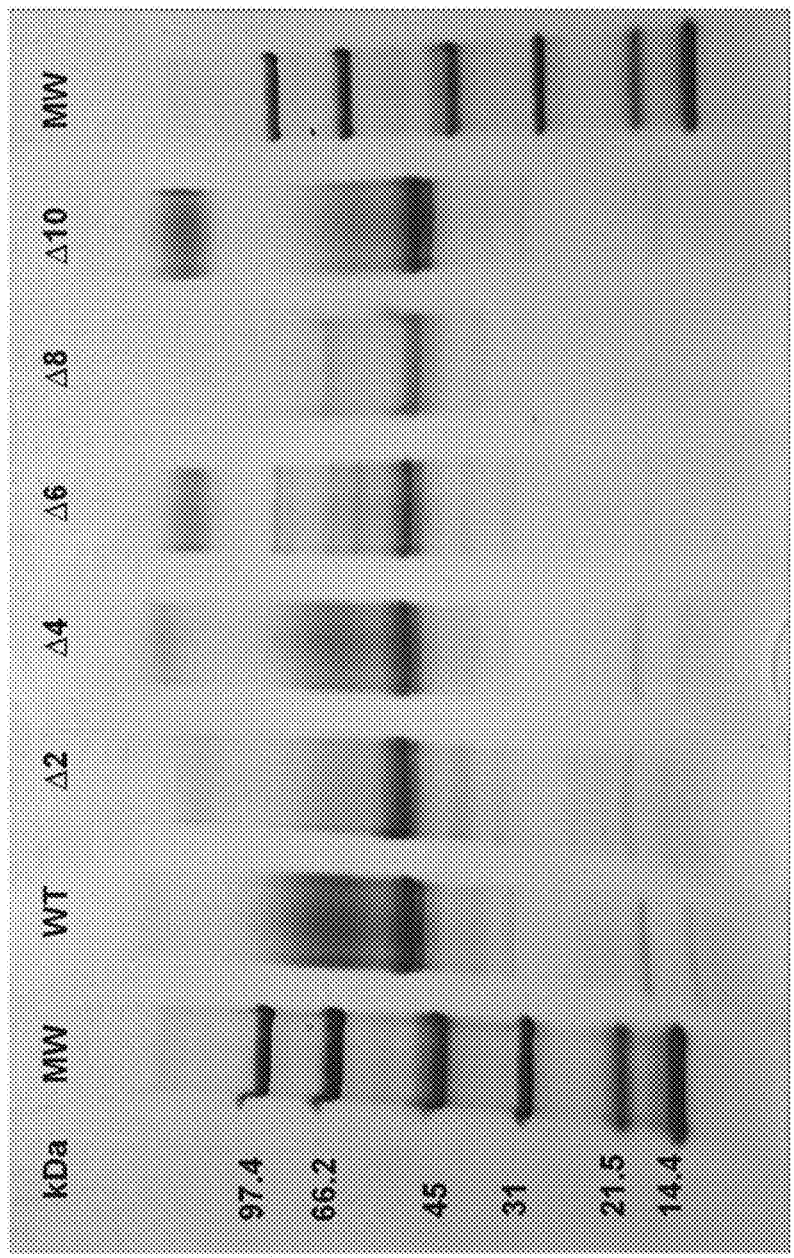
FIG. 3 depicts SDS-PAGE for purification of αGal. Purified samples were run on a 4-20% polyacrylamide gel, under reducing conditions, and stained with Coomassie Brilliant Blue. The contents of the lanes are as follows: molecular weight marker (lane 1 and 8), WT(PC626) (lane 2), Δ2 (PC995) (lane 3), Δ4 (PC897) (lane 4), Δ6 (PC958) (lane 5), Δ8 (PC973) (lane 6), Δ10 (PC960) (lane 7). The minor bands present in the purified fraction are consistent with high molecular weight glycoforms seen previously when WT enzyme was purified from the same *P. pastoris* expression system [53].
Figure 4A:
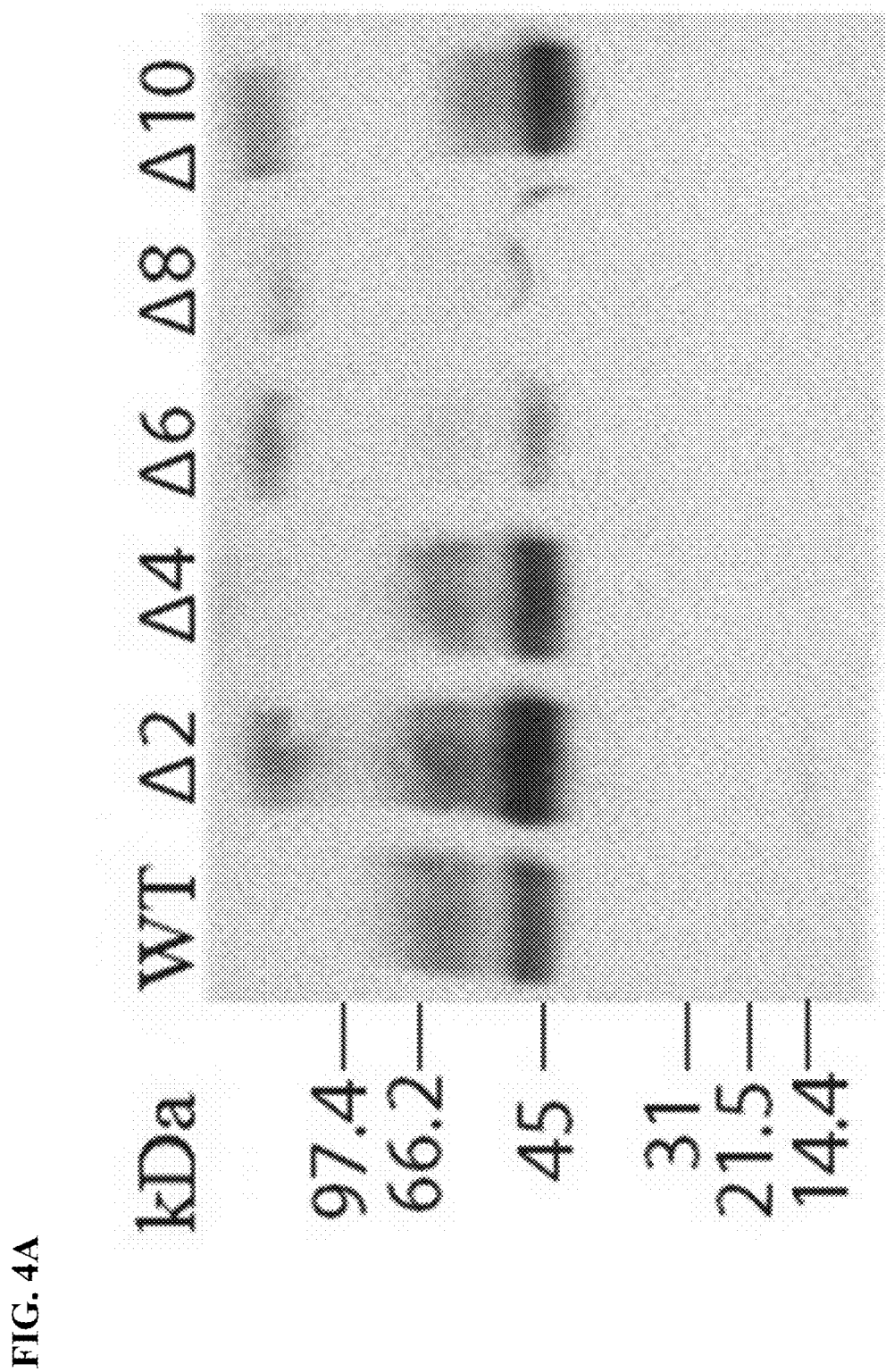
FIGS. 4A-B depict a Western Blot of purified WT and mutant αGal. Purified WT and mutant enzymes were subjected to Western blotting using a polyclonal antibody raised against residues 55-64 and 396-407 of αGal.
Figure 4B:
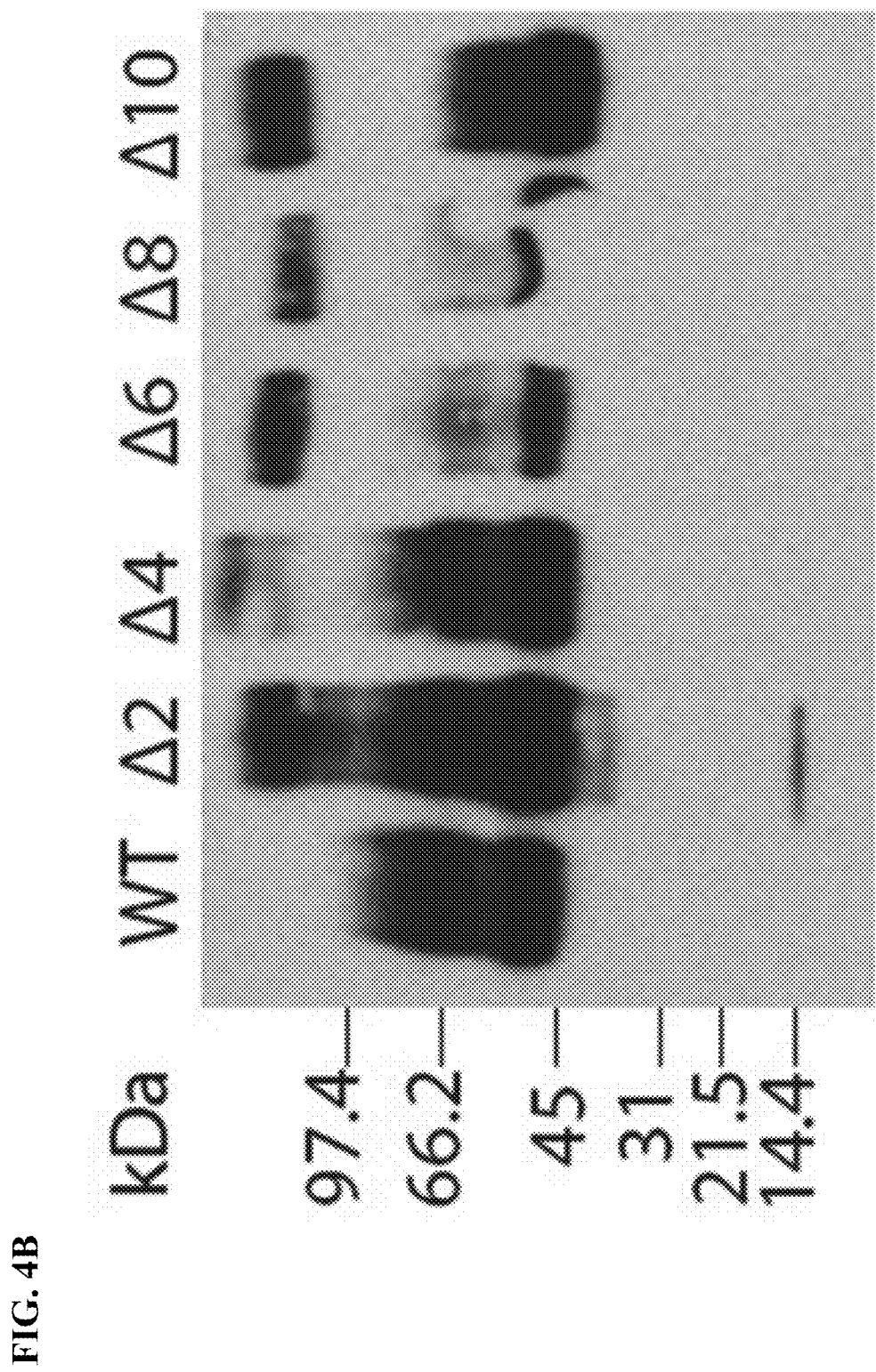

The non-glycosylated form of αGal (41.8 kDa) is purified from cells as multiple glycosylated species with a predominant band of about 50 kDa and multiple higher molecular weight forms that differ in extent of glycosylation (FIG. 3; See Introduction). We have previously demonstrated that high molecular weight glycoforms produced in insect cells and P. pastoris can be identified as derivatives of αGal rather than contaminants and these glycoforms are converted to a single band on SDS gels of about 41.8 kDa with endoglycosidase treatment [49, 50, 53]. In this report we also use a Western blot (FIG. 4) to confirm that the high molecular weight forms seen on SDS gels for the WT and deletion mutants are all glycoforms of αGal. In some cases lower molecular weight species present in purified enzyme preparations can be identified as αGal fragments in Western blots (e.g., FIG. 4, lane 2). We quantitated the distribution of glycoforms in (FIG. 3, FIG. 9) and there is no obvious correlation between the glycosylation pattern and catalytic activity. It is well established that glycosylation affects enzyme stability and enzyme uptake (above) but to our knowledge there is no evidence that the glycosylation pattern affects the catalytic properties of this enzyme.

Example 3. Mass Spectrometry of a Purified Mutant Enzyme

Two possible amino terminal amino acids, glutamate or leucine, could be produced in P. pastoris depending upon the selection of the signal peptidase, Kex2 or Ste13 (FIG. 1). Due to the fact that potential improper amino terminal processing may have an effect on kinetics, we selected one of the purified mutant enzymes (Δ6) for mass spectrometry analysis in order to identify the amino terminal sequence of this enzyme. This analysis also made it possible to provide independent verification of the expected changes in the C-terminal amino acid sequence predicted by in vitro mutagenesis (FIG. 1, 2).

Figure 5A:
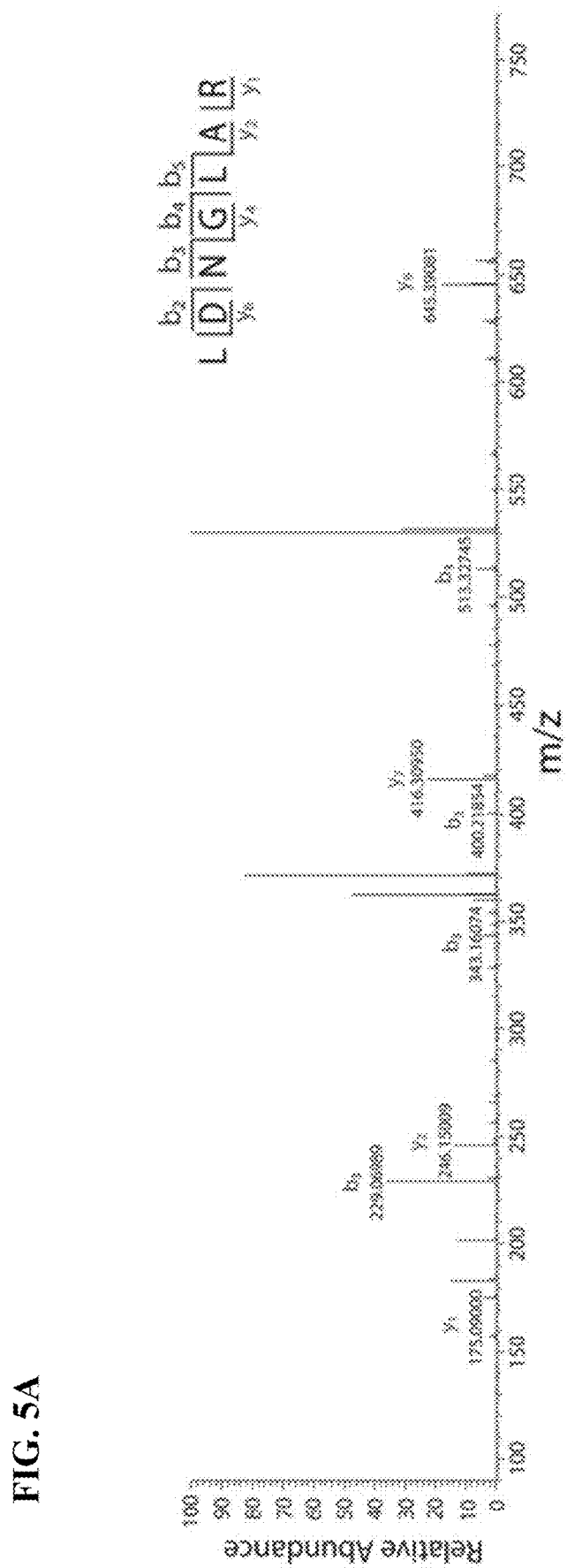
FIGS. 5A-B depict mass spectrometry of purified Δ6 αGal. MS/MS spectra obtained from parental MS ions (FIG. 5A) m/z=379.71 and (FIG. 5B) m/z=1064.03 corresponding to a C-terminal and N-terminal peptide, respectively. Product ion peaks are annotated according to their predicted

The mature form of the enzyme (signal peptide removed; [75]) produced in humans begins with a leucine codon (FIG. 1, 2). Therefore, tandem mass spectrometry following tryptic digestion of the Δ6 αGal purified from P. pastoris could produce tryptic peptides EALDNGLAR or LDNGLAR, depending upon the use of the Kex2 or Ste13 protease sites (FIG. 1, 2). A putative LDNGLAR peak was identified in the MS spectra with an m/z of 379.71, consistent with the (M+2H)2+ state of this peptide, while no peaks consistent with an EALDNGLAR peptide were found. We cannot eliminate what we consider to be the less likely possibility that the failure to detect the EALDNGLAR peptide may be due to the failure of the peptide to ionize in this MS experiment. Further fragmentation of the m/z=379.71 associated peptide peak produced an MS/MS spectrum containing 4 of 7 possible y-ions and 4 of 7 possible b-ions from the expected fragmentation pattern of a hypothetical LDNGLAR peptide (FIG. 5a). This result indicates that the Ste13 signal peptidase of P. pastoris generates an enzyme with an amino terminus identical to the enzyme produced in humans.

Figure 2:
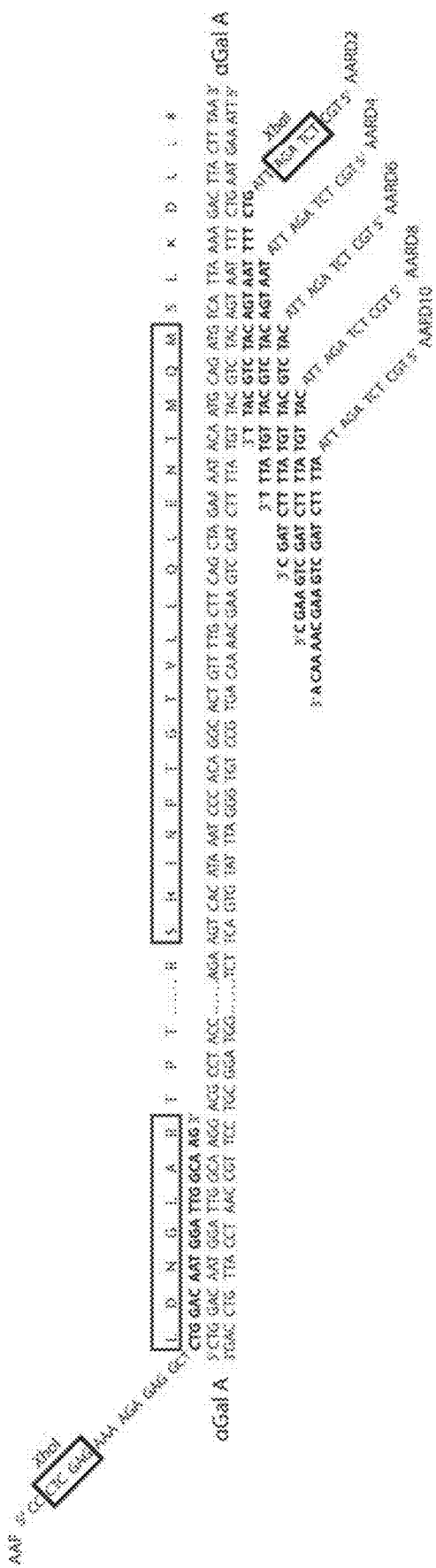
FIG. 2 depicts primers and αGal cDNA used to generate Δ2, Δ4, Δ6, Δ8 and Δ10 mutant cDNAs. DNA primers AAF, AARD2, AARD4, AARD6, AARD8 and AARD10 corresponding to the Δ2, Δ4, Δ6, Δ8 and Δ10 mutants were annealed to the cDNA of mature αGal contained within pMS118 to generate 30 end truncated PCR products for carboxy-terminal deleted enzymes. Primer AAF and primers AARD2 to AARD10 (indicated above) were annealed to the 50 and 30 ends of the cDNA, respectively. Primer AAF contains an XhoI site (indicated above) and partially encodes for a yeast signal peptide (see FIG. 1) to produce a fusion protein targeted for secretion from *P. pastoris*. Primers AARD2 to AARD10 were used to introduce an XbaI site (indicated above) and a premature UAA stop codon via an antisense ATT triplet immediately downstream of nucleotides complementary to αGal (bold font) to produce cDNAs encoding for Δ2, Δ4, Δ6, Δ8, Δ10 mutants. The boxed LDNGLAR and SHINPTGTVLLQLENTMQM protein sequences (indicated above) are peptide fragments that were identified through mass spectrometry of the Δ6 mutant (FIG. 5).
Figure 5B:
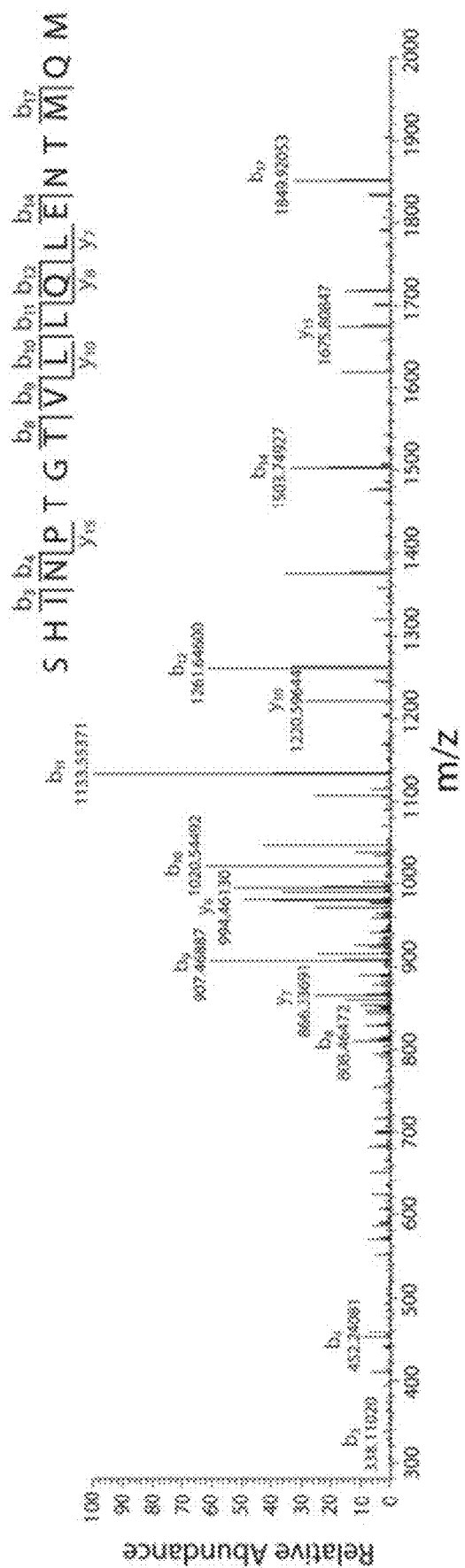

A search for a Δ6 C-terminal tryptic peptide of SHINPTGTVLLQLENTMQM (FIG. 2) yielded a matching MS m/z=1064.03 peak consistent with its (M+2H)2+ state. Further fragmentation also produced an MS/MS spectrum containing 4 of 19 possible y-ions and 9 of 19 possible b-ions consistent with the anticipated sequence (FIG. 5b). This result confirms the predicted C-terminal deletion of 6 amino acids and confirms the efficacy of the mutagenesis protocol used to produce this mutant enzyme.

Thus, the purified Δ6 αGal mutant possesses an N-terminal sequence corresponding to the mature form of αGal and a C-terminal sequence truncated by six amino acids.

Example 4. Thermostability and pH Optima of WT and Deletion Mutants of αGal

Preparations of purified WT and mutant αGal show similar thermostability profiles at 30° C., 40° C., and 50° C., with activity half-lives of 30, 25 and 17 minutes, respectively (FIG. 6). The general trend of these profiles agree with previous results [76]. All enzymes show optimal activity near pH 4.5 (FIG. 7) in accord with previous reports for WT αGal [70, 77-79], and there is no significant difference in the activity optima of purified WT and mutant αGal.

Example 5. Kinetic Analysis of WT and C-Terminal Deletion Mutants

The values for Km and Vmax for WT enzyme (Table 3a) are in accord with published values (Table 5). The range of Km and Vmax values for the enzymes purified from several sources in various laboratories over a period of more than 30 years (Table 5) are in good agreement and the observed subtle variations are in the range expected. However, more precision is expected for measurements recorded for enzymes purified from the same source in a single laboratory at one given time (Table 3a). Substrate saturation curves (FIG. 8a) and the calculated values for Km, Vmax, kcat, and kcat/Km using the MUG substrate (Table 3a) reveal differences in the enzyme activity of the mutants compared to WT. Deletions of 2, 4, 6 and 10 amino acids approximately double the kcat/Km (0.8 to 1.7-fold effect; 29/34.4=0.8 and 58.3/34.4=1.7) while a deletion of 8 amino acids decreases the kcat/Km (7.2-fold effect; 34.4/4.78=7.2). There are corresponding changes in the Vmax values and deletions of 2, 4, 6 and 10 amino acids approximately double the Vmax (1.5 to 2.2-fold effect; 4.89/3.36=1.5 and 7.29/3.36=2.2) while a deletion of 8 amino acids decreases the Vmax (4.5-fold effect; 3.36/0.742=4.5). There are also smaller differences in the Km values of the C-terminal deletion mutants compared to the WT (Table 3a). The Vmax data presented for the Δ8 (0.742±0.21) and WT (3.36±0.29) are derived from multiple assays from three and two independent enzyme samples, respectively, and this indicates the reliability of this data and adds strength to the interpretations of the data from the single enzyme preparations used for the other deletion mutants.

Without wishing to be bound by theory, the effects of the C-terminal deletions on the kinetic properties of the enzyme using the artificial substrate MUG (Table 3a) could be due to alterations in the inherent catalytic mechanism of the enzyme [85]. Alternatively, the altered kinetic properties could be due to changes in the affinity of the enzyme for specific structural components of the artificial substrate, MUG. In this context, it is of interest to measure these kinetic parameters with an alternative substrate such as PNPαGal. The results (Table 3b, FIG. 8b) indicate that there are similar changes in kinetic parameters using PNPαGal as the substrate, including increases (2.2-fold effect; 9.18/4.18=2.2) and decreases (3.2-fold effect; 4.18/1.31=3.2) in the kcat/Km for the specific C-terminal deletion mutants (Δ10 and Δ8, respectively). Taken together, these results suggest that the C-terminal deletions likely affect some aspect of the inherent catalytic mechanism of the enzyme.

TABLE 3

Table 3. Values of $K_m$, $V_{max}$, $k_{cat}$ and the specificity constant ($k_{cat}/K_m$) for WT and C-Terminal Deletion Mutants of αGal.

| Comments | $K_m$ (mM) | $V_{max}$ (mmole/hr/mg) | $k_{cat}$ (s$^{-1}$) | $k_{cat}/K_m$ (mM$^{-1}$s$^{-1}$) |
|---|---|---|---|---|
| A) MUG | | | | |
| WT | 2.44 ± 0.44 | 3.36 ± 0.29 | 84.0 | 34.4 |
| Δ2 | 4.52 ± 0.62 | 5.56 ± 0.73 | 139 | 30.8 |
| Δ4 | 3.51 ± 0.29 | 7.29 ± 0.74 | 182 | 51.9 |
| Δ6 | 4.21 ± 0.52 | 4.89 ± 0.32 | 122 | 29.0 |
| Δ8 | 3.89 ± 0.27 | 0.742 ± 0.21 | 18.6 | 4.78 |
| Δ10 | 2.96 ± 0.29 | 6.90 ± 0.71 | 173 | 58.3 |
| B) PNPαGal | | | | |
| WT | 15.0 ± 2.0 | 2.51 ± 0.17 | 62.8 | 4.18 |
| Δ2 | 13.3 ± 1.2 | 5.14 ± 0.82 | 128 | 9.65 |
| Δ4 | 15.7 ± 1.0 | 5.74 ± 0.39 | 143 | 9.13 |
| Δ6 | 13.4 ± 1.1 | 1.89 ± 0.23 | 47.3 | 3.53 |
| Δ8 | 13.0 ± 1.5 | 0.68 ± 0.08 | 17.0 | 1.31 |
| Δ10 | 17.0 ± 3.0 | 6.24 ± 0.12 | 156 | 9.18 |

The values given are for the human enzyme purified from P. pastoris and assayed in triplicate followed by Lineweaver-Burk and non-linear regression analysis. Comparison of both Lineweaver-Burk and non-linear regression kinetic parameters show good general agreement (data not shown). Non-linear regression results are displayed above. The $k_{cat}$ was calculated using 90 kDa as the MW of αGal.
A) MUG was used as the substrate for enzyme assay. Mean and standard deviation measurements are from multiple assays of three independent enzyme preparation for the Δ8 enzyme, two independent enzyme preparations for the WT enzyme, and single enzyme preparations for the other mutant enzymes.
B) PNPαGal was used as the substrate for enzyme assay.
Doi: 10.1371/journal.pone.0118341.t003

TABLE 4

Table 4. Purification on Table for WT αGal Expressed in P. pastoris.

| Step | Total Protein (mg) | Total Activity (Units × 10$^6$) | Specific Activity (Units/mg × 10$^3$) | Purification (Fold) | Yield (%) |
|---|---|---|---|---|---|
| Supernatant | 10,928 | 134 | 610 | 1.0 | 100 |
| Con A Pool | 138 | 30.4 | 221 | 18.1 | 22.8 |
| Thio-Gal Pool | 4.18 | 15.7 | 3,771 | 309 | 11.8 |

Note.
5 mM MUG was used as the substrate for enzyme assay.
Doi: 10.1371/journal.pone.011834.t004
PLOS ONE | DOI: 10.1371/journal.pone.0118341 Feb. 26, 2015 10/26

TABLE 5

Table 5. Literature Values for $K_m$ and $V_{max}$ for the WT Human αGal.

| $K_m$ (mM) | $V_{max}$ (mmole/hr/mg) | Source | Reference | Year |
|---|---|---|---|---|
| 1.6 | NA | Placenta | [80] | 1978 |
| 2.9 | 1.7 | Liver | [78] | 1979 |
| 1.9 | NA | Plasma | [60] | 1979 |
| 2.5 | NA | Spleen | [60] | 1979 |
| 2.0 | 2.8 | Spleen | [69] | 1981 |
| 2.3 | 2.3 | Sf9 insect cells | [81] | 2000 |
| 2.0 | 4.8 | Replagal | [24] | 2003 |
| 2.0 | 4.8 | Fabrazyme | [24] | 2003 |
| 4.0 | 3.3 | Fabrazyme | [82] | 2009 |
| 2.8 | 2.6 | COS-7 cells | [83] | 2007 |
| 4.5 | 3.3 | COS-7 cells | [84] | 2011 |

Note.
The values given are for the human enzyme purified directly from human tissues or from the indicated recombinant sources. Replagal is produced in human foreskin fibroblasts and Fabrazyme is produced in CHO cells. The average from these literature values are 2.6 ± 0.9 mM ($K_m$) and 3.2 ± 1.1 mmole/hr/mg ($V_{max}$).
NA: not available. MUG was used as the substrate to determine the $K_m$ and $V_{max}$ values.
Doi: 10.1371/journal.pone.0118341.t005

TABLE 6

Table 6. Literature Values of $K_m$, $k_{cat}$, and the specificity constant ($k_{cat}/K_m$) for Glycosyl Hydrolase Family 27 αGal Enzymes.

| Pubmed Accession code | Genus and species | Colloquial name | $K_m$ (mM) | $k_{cat}$ (s$^{-1}$) | $k_{cat}/K_m$ (mM$^{-1}$s$^{-1}$) | Relative $K_{cat}/K_m$ | Ref. |
|---|---|---|---|---|---|---|---|
| NP_000160 | *Homo sapiens* | Human | 6.88 | 37.8 | $5.49 \times 10^3$ | 1 | [95] |
| NP_038491 | *Mus musculus* | Mouse | 1.40 | N/A | N/A | N/A | [96] |
| WP_004844583.1 | *Ruminococcus gnavus* | Bacteria | 1.80 | 30.1 | $1.67 \times 10^4$ | 3 | [92] |
| AAC99325 | *Saccharopolyspora erythraea* | Bacteria | 0.650 | 23.3* | $3.58 \times 10^4$ | 6 | [98] |
| P41947 | *Saccharomyces cerevisiae* | Yeast | 4.50 | 286 | $6.36 \times 10^4$ | 12 | [99] |
| BAB83765 | *Clostridium josuil* (Catalytic Domain) | Bacteria | 0.810 | 61.9* | $7.64 \times 10^4$ | 14 | [100] |
| AAG24511 | *Phanerochaete chrysosporium* | Fungus | 0.198 | 272 | $1.37 \times 10^6$ | 250 | [101] |

Note.
PNP αGal substrate was used to calculate kinetic values. Family 27 enzymes include the human αGal and related enzymes in the CAZy database [102] that are most closely related as indicated by BLAST analysis [94].
*$k_{cat}$ values for *S. erythraea* and *C. josuil* were calculated based on the reported $V_{max}$, and molecular weights.
Doi: 10.1371/journal.pone.0118341.t006

TABLE 7

39.X, WT aGal from FR41

| Aliquot# | Contents | Date | Page# | Vol (mL) | U/mL | Total Units | mg/mL | mg |
|---|---|---|---|---|---|---|---|---|
| 39.1 | Sup from FR41 | | | 7,000 | 72,825 | 509,775,000 | | |
| 39.2 | Sup after Centrifugation | 26-Jan | | 5,500 | 91,575 | 503,662,500 | | |
| 39.3 | Sup after diafiltration + AC + buffer exchange to wash buffer | 27-Jan | αIII-240 | 438 | 304,800 | 133,502,400 | 25.0 | 10,935 |
| 39.4 | pool B2-E3 (FT load + wash ConA) | 24-Feb | | 1,100 | 20,280 | 22,308,000 | | |
| 39.5 | pool A4-F1 + G2-65 (E1-E4, E6 ConA) | 5-Mar | αIII-243 | 1,800 | 26,640 | 47,952,000 | | |
| 39.6 | 39.5 AC + buffer exchange to binding | 5-Mar | αIII-243 | 150 | 202,650 | 30,397,500 | 0.919 | 138 |
| 39.7 | Thiogal Elution tube A6 | 15-Mar | MMII70 | 14 | 95775 | 1340850 | 0.0504 | 0.706 |
| 39.8 | Thiogal Elution tube A7 | 15-Mar | MMII70 | 14 | 109725 | 1536150 | 0.0323 | 0.452 |
| 39.9 | Thiogal Elution tube A8 | 15-Mar | MMII70 | 14 | 118,725 | 1,662,150 | 0.0168 | 0.235 |
| 39.10 | Thiogal Elution A5 | 29-Mar | αIII-243 | 4 | 110,100 | 440,400 | 0.0336 | 0.134 |
| 39.11 | Thiogal Elution A9 | 29-Mar | αIII-243 | 14 | 101,475 | 1,420,650 | 0.0135 | 0.189 |
| 39.12 | Thiogal Elution A10 | 29-Mar | αIII-243 | 14 | 104,250 | 1,459,500 | 0.0109 | 0.153 |
| 39.13 | Thiogal Elution A11 | 29-Mar | αIII-243 | 14 | 2,823 | 39,517 | | |
| 39.14 | Thiogal Elution A12 | 29-Mar | αIII-243 | 14 | 2,065 | 28,908 | | |
| 39.15 | Thiogal pool Tubes A4-B12 | | | 240 | 65,625 | 6,969,600 | 0.017 | 4.176 |
| 39.16 | Thiogal Elution Tube A5 2 mL----->47 uL | 3-Apr | αIII-244 | 0.0470 | | | 2.780 | 0.131 |
| 39.17 | Thiogal Elution Tube A6 1.5 mL---->41 uL | 3-Apr | αIII-244 | 0.0410 | | | 3.530 | 0.145 |
| 39.18 | Thiogal Elution Tube A7 2 mL------>45 uL | 3-Apr | αIII-244 | 0.0450 | | | 4.270 | 0.192 |
| 39.19 | Thiogal Elution Tube A8 3.5 mL---->39 uL | 3-Apr | αIII-244 | 0.0390 | | | 5.450 | 0.213 |
| 39.20 | Thiogal pool 39.15 AC + buffer exchange to | 4-Apr | αIII-244 | 60.0 | 277,050 | 16,623,000 | 0.0366 | 2.196 |
| 39.21 | 1700 uL of 39.20 -----> 39 uL of 39.21 | 5-Apr | αIII-244 | 0.0390 | | | 1.938 | 0.0756 |
| 39.22 | 500 uL of 39.6 ------> 51 uL of 39.22 | 5-Apr | αIII-244 | 0.0510 | | | 5.560 | 0.284 |
| 39.23 | 500 uL of 39.20 -----> 200 uL of 39.23 | 2-May | αIII-244 | 0.212 | | | | |
| 39.24 | 250 uL of 39.20 -----> 70 uL of 39.24 | 9-May | ES219 | 0.070 | | | | |

The invention claimed is:

1. A method of purifying recombinant alpha-galactosidase A, said method comprising:
   (a) obtaining a supernatant from cells recombinantly expressing alpha-galactosidase A grown in a cell culture medium comprising non-precipitating phosphate;
   (b) contacting said supernatant with a chromatography media, wherein said chromatography media comprises media that binds α-D-mannopyranosyl or α-D-glucopyranosyl; and
   (c) eluting alpha-galactosidase A from said chromatography media to generate an eluate comprising alpha-galactosidase A, wherein said eluting comprises at least one elution pause between 4 and 16 hours.

2. The method of claim 1, wherein said supernatant is clarified prior to contacting the chromatography media.

3. The method of claim 1, wherein said non-precipitating phosphate comprises sodium hexametaphosphate.

4. The method of claim 1, wherein said chromatography media comprises Concanavalin A.

5. The method of claim 1, wherein said eluate is contacted with a chromatography media comprising D-galactose.

6. The method of claim 1, wherein said elution pause is between 10 and 14 hours.

7. The method of claim 1, wherein the eluate is subject to diafiltration.

8. The method of claim 1, wherein the eluate is subject to buffer exchange.

9. The method of claim 1, wherein the alpha-galactosidase A is truncated.

* * * * *

UNITED STATES PATENT AND TRADEMARK OFFICE
CERTIFICATE OF CORRECTION

PATENT NO. : 10,851,360 B2
APPLICATION NO. : 15/912075
DATED : December 1, 2020
INVENTOR(S) : David H. Calhoun et al.

It is certified that error appears in the above-identified patent and that said Letters Patent is hereby corrected as shown below:

In the Specification

Column 17/18, Third Line in Table 6:
Now reads:
"WP_004844583.1 *Ruminococcus gnavus* Bacteria 1.80 30.1 1.67 × $10^4$ 3 [92]"
Should read:
-- WP_004844583.1 *Ruminococcus gnavus* Bacteria 1.80 30.1 1.67 × $10^4$ 3 [97] --

Column 17/18, Eighth Line in Table 7:
Now reads:
"39.5 Pool A4-F1 + G2 – 65 (E1-"
Should read:
-- 39.5 Pool A4-F1 + G2 – G5 (E1- --

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*